United States Patent [19]

Attwood et al.

[11] Patent Number: 5,118,694

[45] Date of Patent: Jun. 2, 1992

[54] BENZOPYRAN DERIVATIVES

[75] Inventors: Michael R. Attwood, Hitchin; Philip S. Jones; Sally Redshaw, both of Stevenage, all of England

[73] Assignee: Hoffmann-La Roche Inc., Nutley, N.J.

[21] Appl. No.: 580,881

[22] Filed: Sep. 11, 1990

Related U.S. Application Data

[62] Division of Ser. No. 210,692, Jun. 23, 1988, Pat. No. 4,971,982.

[30] Foreign Application Priority Data

Jul. 6, 1987 [GB] United Kingdom ............... 8715839
Apr. 29, 1988 [GB] United Kingdom ............... 88102124

[51] Int. Cl.⁵ .................... A61K 31/44; A61K 31/47;
A61K 31/35; C07D 405/04
[52] U.S. Cl. .................................. 514/337; 514/254;
514/256; 514/312; 514/314; 514/456; 544/298;
544/333; 544/405; 546/153; 546/167; 546/196;
549/467; 549/469
[58] Field of Search ............ 544/298, 333, 405;
546/153, 167, 196; 549/467, 469; 514/254, 256,
314, 312, 337, 456

[56] References Cited

U.S. PATENT DOCUMENTS

| | | | |
|---|---|---|---|
| 4,181,722 | 1/1980 | Beranger et al. | 544/364 |
| 4,391,821 | 7/1983 | Korbonits et al. | 549/401 |
| 4,443,459 | 4/1984 | Yano et al. | 546/269 |
| 4,563,468 | 1/1986 | Batchelor et al. | 514/337 |
| 4,631,282 | 12/1986 | Cassidy | 514/254 |

FOREIGN PATENT DOCUMENTS

| | | |
|---|---|---|
| 0107423 | 10/1983 | European Pat. Off. |
| 0218373 | 9/1986 | European Pat. Off. |
| 298452 | 1/1989 | European Pat. Off. |
| 2390445 | 12/1978 | France . |
| 2496102 | 6/1982 | France . |
| 1151209 | 5/1982 | U.S.S.R. . |

OTHER PUBLICATIONS

Nakatsubo et al., CA 108-5825f (1988).
EP 76075, Derwent No. 83-35014K/15 (1983).
EP 250077, Derwent No. 88-022640/04 (1987).
CA 35760y, vol. 75, 1971.
CA 101:90725w 1984.

*Primary Examiner*—Cecilia Shen
*Attorney, Agent, or Firm*—George M. Gould; William G. Isgro; Ellen C. Coletti

[57] ABSTRACT

Compounds of the formula

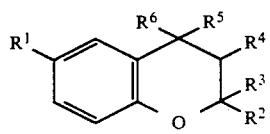

wherein $R^1$ is hydrogen, halogen, trifluoromethyl, nitro, cyano, lower alkyl, lower alkoxycarbonyl, lower alkylthio, lower alkylsulphonyl, lower alkanoyl, aroyl, carbamoyl, mono(lower alkyl)carbamoyl or di(lower alkyl)carbamoyl, $R^2$ is hydrogen, lower alkyl or phenyl, $R^3$ is hydrogen or lower alkyl, $R^4$ and $R^5$ each is hydrogen or $R^4$ is hydroxy and $R^5$ is hydrogen or $R^4$ and $R^5$ together are a carbon-carbon bond and $R^6$ is an aryl or N-heteroaryl group carrying a hydroxy group in the 2-position or, in the case of a N-heteroaryl group, also a N-oxide group in the 2-position, and pharmaceutically acceptable acid addition salts of these compounds of formula I which are basic, possess pronounced potassium channel activating activity and can be used as medicaments, particularly in the control or prevention of hypertension, congestive heart failure, angina pectoris, peripheral and cerebral vascular disease and smooth muscle disorders.

16 Claims, No Drawings

BENZOPYRAN DERIVATIVES

This is a division of U.S. application Ser. No. 07/210,692, filed Jun. 23, 1988, now U.S. Pat. No. 4,971,982, filed on Nov. 20, 1990.

BRIEF SUMMARY OF THE INVENTION

The invention is related to benzopyran derivatives of the formula I

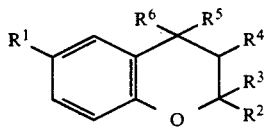

wherein $R^1$ is hydrogen, halogen, trifluoromethyl, nitro, cyano, lower alkyl, lower alkoxycarbonyl, lower alkylthio, lower alkylsulphonyl lower alkanoyl, aroyl, carbamoyl, mono(lower alkyl)carbamoyl or di(lower alkyl)carbamoyl, $R^2$ is hydrogen, lower alkyl or phenyl, $R^3$ is hydrogen or lower alkyl, $R^4$ and $R^5$ each is hydrogen or $R^4$ is hydroxy and $R^5$ is hydrogen or $R^4$ and $R^5$ together are a carbon-carbon bond and $R^6$ is an aryl or N-heteroaryl group carrying a hydroxy group in the 2-position or, in the case of a N-heteroaryl group, also a N-oxide group in the 2-position,
and pharmaceutically acceptable acid addition salts of these compounds of formula I which are basic.

These benzopyran derivatives are novel and possess valuable pharmacodynamic properties.

Objects of the present invention are: The compounds of formula I above and the aforementioned salts thereof per se, a process and intermediates for their manufacture, medicaments containing the compounds of formula I and their aforementioned salts, the use of the compounds of formula I and their aforementioned salts in the control or prevention of illnesses, especially in the control or prevention of hypertension, congestive heart failure, angina pectoris, peripheral and cerebral vascular disease and smooth muscle disorders, and the use of the compounds of formula I and their aforementioned salts in the preparation of a medicament for the control or prevention of hypertension, congestive heart failure, angina pectoris, peripheral and cerebral vascular disease and smooth muscle disorders.

DETAILED DESCRIPTION OF THE INVENTION

The invention is related to benzopyran derivatives of the formula

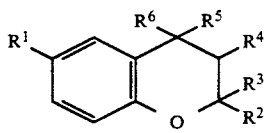

wherein $R^1$ is hydrogen, halogen, trifluoromethyl, nitro, cyano, lower alkyl, lower alkoxycarbonyl, lower alkylthio, lower alkylsulphonyl, lower alkanoyl, aroyl, carbamoyl, mono(lower alkyl)carbamoyl or di(lower alkyl)carbamoyl, $R^2$ is hydrogen, lower alkyl or phenyl, $R^3$ is hydrogen or lower alkyl, $R^4$ and $R^5$ each is hydrogen or $R^4$ is hydroxy and $R^5$ is hydrogen or $R^4$ and $R^5$ together are a carbon-carbon bond and $R^6$ is an aryl or N-heteroaryl group carrying a hydroxy group in the 2-position or, in the case of a N-heteroaryl group, also a N-oxide group in the 2-position,
and pharmaceutically acceptable acid addition salts of these compounds of formula I which are basic.

These benzopyran derivatives are novel and possess valuable pharmacodynamic properties.

Objects of the present invention are: The compounds of formula I above and the aforementioned salts thereof per se, a process and intermediates for their manufacture, medicaments containing the compounds of formula I and their aforementioned salts, the use of the compounds of formula I and their aforementioned salts in the control or prevention of illnesses, especially in the control or prevention of hypertension, congestive heart failure, angina pectoris, peripheral and cerebral vascular disease and smooth muscle disorders, and the use of the compounds of formula I and their aforementioned salts in the preparation of a medicament for the control or prevention of hypertension, congestive heart failure, angina pectoris, peripheral and cerebral vascular disease and smooth muscle disorders.

As used in this specification, the term "lower alkyl", alone or in combination, means a straight-chain or branched-chain alkyl group containing from 1 to 7, preferably from 1 to 4, carbon atoms such as methyl, ethyl, n-propyl, isopropyl, n-butyl, isobutyl, s-butyl, t-butyl, n-pentyl and the like. Methylthio, ethylthio and the like are examples of lower alkylthio groups and methylsulphonyl, ethylsulphonyl and the like are examples of lower alkylsulphonyl groups. The term "lower alkoxy", alone or in combination, means a lower alkyl group as defined above which is bonded via an oxygen atom. Examples of lower alkoxy groups are methoxy, ethoxy n-propoxy, isopropoxy, n-butoxy and the like and examples of lower alkoxycarbonyl groups are methoxycarbonyl, ethoxycarbonyl and the like. The term "lower alkanoyl" means a primary or secondary alkanoyl group containing up to 7 carbon atoms such as acetyl, propionyl, butyryl, isobutyryl and the like. The term "aroyl" means the benzoyl group or a substituted benzoyl group, for example a nitrobenzoyl group such as p-nitrobenzoyl or a halobenzoyl group such as o-, m- or p-iodobenzoyl. Methylcarbamoyl, ethylcarbamoyl and the like are examples of mono(lower alkyl)carbamoyl groups and dimethylcarbamoyl, diethylcarbamoyl and the like are examples of di(lower alkyl)carbamoyl groups.

The aryl group denoted by $R^6$ can be a monocyclic or bicyclic aryl group which, in addition to the hydroxy group in the 2-position, can optionally contain one or more additional substituents selected from halogen, cyano and lower alkyl. Examples of such aryl groups are 2-hydroxyphenyl, 4-chloro-2-hydroxyphenyl, 2-hydroxy-6-methylphenyl, 4-cyano-2-hydroxyphenyl, 2-hydroxynaphthyl and the like. The N-heteroaryl group denoted by $R^6$ can be a monocyclic or bicyclic N-heteroaryl group which contains one or more nitrogen atoms and which, in addition to the hydroxy or N-oxide group in the 2-position, can optionally contain one or more additional substituents selected from halogen, amino, hydroxy, benzyloxy, phenyl, (lower alkyl)-phenyl, lower alkyl, lower alkoxy and lower alkoxycarbonyl. Examples of such N-heteroaryl groups are 2-hydroxy-3-pyridyl, 2-hydroxy-4-methyl-3-pyridyl, 3-hydroxy-4-pyridyl 2-pyridyl N-oxide, 3-chloro-2-pyridyl N-oxide, 4-chloro-2-pyridyl N-oxide 5-chloro-2-pyridyl N-oxide, 6-chloro-2-pyridyl N-oxide, 5-amino-2-pyridyl N-oxide, 6-amino-2-pyridyl N-oxide, 5-hydroxy-2-pyridyl N-oxide, 5-benzyloxy-2-pyridyl N-oxide 5-phenyl-2-pyridyl N-oxide, 5-(4-methylphenyl)-2-pyridyl N-oxide, 3-methyl-2-pyridyl N-oxide, 4/methyl-2-pyridyl N-oxide, 5-methyl-2-pyridyl N-oxide, 6-methyl-2-pyridyl N-oxide, 4-methoxy-2-pyridyl N-oxide, 5-methoxycarbonyl-2-pyridyl N-oxide, 2-pyrazinyl 1-oride, 2-pyrimidinyl 1-oxide, 6-pyrimidinyl 1-oxide 2-quinolyl 1-oxide and the like.

It will be appreciated that, when $R^2$ and $R^3$ in formula I are different, the compounds can exist in racemic or optically active form. Further, the compounds of formula I can exist in racemic or optically active form when $R^4$ and $R^5$ each is hydrogen or when $R^4$ is hydroxy and $R^5$ is hydrogen. Thus, when $R^2$ and $R^3$ are different and either $R^4$ and $R^5$ each is hydrogen or $R^4$ is hydroxy and $R^5$ is hydrogen the compounds of formula I can exist in different diastereomeric forms. Further, cis/trans isomerism can occur in those compounds of formula I in which $R^4$ is hydroxy and $R^5$ is hydrogen. When $R^6$ in formula I is a N-heteroaryl group carrying a hydroxy group in the 2-position, the compounds can exist in tautomeric form. The invention includes within its scope all of these possible forms.

A particular sub-group of compounds of formula I comprises those in which $R^1$ is hydrogen, halogen, nitro, cyano, lower alkyl, lower alkoxycarbonyl, lower alkylthio, lower alkylsulphonyl, lower alkanoyl, carbamoyl, mono(lower alkyl)carbamoyl or di(lower alkyl)carbamoyl, $R^2$ and $R^3$ each is hydrogen or lower alkyl and $R^4$ and $R^5$ each is hydrogen or together are a carbon-carbon bond.

In the compounds provided by the invention, preferably $R^1$ is nitro, cyano or lower alkanoyl, especially nitro, cyano or acetyl. $R^2$ and $R^3$ each preferably is lower alkyl, especially methyl. Preferably, $R^4$ and $R^5$ each is hydrogen or $R^4$ and $R^5$ together are a carbon-carbon bond. $R^6$ preferably is a N-heteroaryl group carrying a N-oxide group in the 2-position, especially a 2-pyridyl N-oxide group which is optionally substituted by halogen, amino, hydroxy, benzyloxy, phenyl, (lower alkyl)-phenyl, lower alkyl, lower alkoxy or lower alkoxycarbonyl.

From the above it will be appreciated that especially preferred compounds of formula I are those in which $R^1$ is nitro, cyano or acetyl, $R^2$ and $R^3$ each is methyl, $R^4$ and $R^5$ each is hydrogen or $R^4$ and $R^5$ together are a carbon-carbon bond and $R^6$ is a 2-pyridyl N-oxide group which is optionally substituted by halogen, amino, hydroxy, benzyloxy, phenyl, (lower-alkyl)-phenyl, lower alkyl, lower alkoxy or lower alkoxycarbonyl.

Particularly preferred compounds of formula I are:
2-(3,4-dihydro-2,2-dimethyl-6-nitro-2H-1-benzopyran-4-yl)pyridine N-oxide,
2-(6-acetyl-3,4-dihydro-2,2-dimethyl-2H-1-benzopyran-4-yl)pyridine N-oxide,
2-(6-cyano-3,4-dihydro-2,2-dimethyl-2H-1-benzopyran-4-yl)pyridine N-oxide and
2-(6-cyano-3,4-dihydro-2,2-dimethyl-2H-1-benzopyran-4-yl)-5-phenylpyridine N-oxide.

Other preferred compounds of formula I are:
2-(6-acetyl-3,4-dihydro-2,2-dimethyl-2H-1-benzopyran-4-yl)-3-methylpyridine N-oxide,
2-(3,4-dihydro-2,2-dimethyl-6-nitro-2H-1-benzopyran-4-yl)-3-methylpyridine N-oxide,
2-(6-cyano-2,2-dimethyl-2H-1-benzopyran-4-yl)pyridine N-oxide,
2-(3,4-dihydro-2,2-dimethyl-2H-1-benzopyran-4-yl)pyridine N-oxide,
2-(3,4-dihydro-2,2-dimethyl-6-methylthio-2H-1-benzopyran-4-yl)pyridine N-oxide,
2-(3,4-dihydro-2,2-dimethyl-6-methylsulphonyl-2H-1-benzopyran-4-yl)pyridine N-oxide,
2-(2.2-dimethyl-2H-1-benzopyran-4-y])pyridine N-oxide.
2-(6-bromo-3,4-dihydro-2,2-dimethyl-2H-1-benzopyran-4-yl)pyridine N-oxide,
2-[6-(methoxycarbonyl)-2,2-dimethyl-2H-1-benzopyran-4-yl]pyridine N-oxide,
2-[3,4-dihydro-6-(methoxycarbonyl)-2,2-dimethyl-2H-1-benzopyran-4-yl]pyridine N-oxide,
2-(6-carbamoyl-3,4-dihydro-2,2-dimethyl-2H-1-benzopyran-4-yl)pyridine N-oxide,
2-(6-cyano-3,4-dihydro-2,2-dimethyl-2H-1-benzopyran-4yl)pyrimidine 1-oxide,
2-(6-cyano-2,2-dimethyl-2H-1-benzopyran-4-yl)quinoline 1-oxide,
2-(6-cyano-3,4-dihydro-2,2-dimethyl-2H-1-benzopyran-4-yl)quinoline 1-oxide,
4-(2-hydroxyphenyl)-2,2-dimethyl-2H-1-benzopyran-6-carbonitrile,
4-(5-cyano-2-hydroxyphenyl)-2,2-dimethyl-2H-1-benzopyran-6-carbonitrile and
3-(6-cyano-3,4-dihydro-2,2-dimethyl-2H-1-benzopyran-4-yl)-2(1H)-pyridone.

Examples of other interesting compounds of formula I are:
2-(6-chloro-3,4-dihydro-2,2-dimethyl-2H-1-benzopyran-4-yl)pyridine N-oxide,
2-(2,2,6-trimethyl-2H-1-benzopyran-4-yl)pyridine N-oxide,
2-[6-(trifluoromethyl)-2,2-dimethyl-2H-1-benzopyran-4-yl]pyridine N-oxide,
2-[6-(t-butyl)-3,4-dihydro-2,2-dimethyl-2H-1-benzopyran-4-yl]pyridine N-oxide,
2-(6-benzoyl-3,4-dihydro-2,2-dimethyl-2H-1-benzopyran-4-yl)pyridine N-oxide,
2-[3,4-dihydro-2,2-dimethyl-6-(4-nitrobenzoyl)-2H-1-benzopyran-4-yl]pyridine N-oxide,
2-[3,4-dihydro-2,2-dimethyl-6-(2-iodobenzoyl)-2H-1-benzopyran-4-yl]pyridine N-oxide,
2-[3,4-dihydro-2,2-dimethyl-6-(3-iodobenzoyl)-2H-1-benzopyran-4-yl]pyridine N-oxide,
2-[3,4-dihydro-2,2-dimethyl-6-(4-iodobenzoyl)-2H-1-benzopyran-4-yl]pyridine N-oxide,
2-(6-cyano-2-ethyl-2-methyl-2H-1-benzopyran-4-yl)pyridine N-oxide,
2-(6-acetyl-2-methyl-2H-1-benzopyran-4-yl)pyridine N-oxide,
2-chloro-6-(6-cyano-3,4-dihydro-2,2-dimethyl-2H-1-benzopyran-4-yl)pyridine N-oxide,
4-chloro-2-(6-cyano-3,4-dihydro-2,2-dimethyl-2H-1-benzopyran-4-yl)pyridine N-oxide,
2-(6-cyano-3,4-dihydro-2,2-dimethyl-2H-1-benzopyran-4-yl)-4-methoxypyridine N-oxide,
2-amino-6-(6-cyano-2,2-dimethyl-2H-1-benzopyran-4-yl)pyridine N-oxide,
2-amino-6-(6-cyano-3,4-dihydro-2,2-dimethyl-2H-1-benzopyran-4-yl)pyridine N-oxide,
2-(6-cyano-3,4-dihydro-2,2-dimethyl-2H-1-benzopyran-4-yl)-6-methylpyridine N-oxide,
2-(6-cyano-2,2-dimethyl-2H-1-benzopyran-4-yl)-4-methylpyridine N-oxide, 2-(6-cyano-3,4-dihydro-2,2-dimethyl-2H-1-benzopyran-4-yl)-4-methylpyridine N-oxide,
2-(6-cyano-3,4-dihydro-2 2-dimethyl-2H-1-benzopyran-4-yl)-5-(methoxycarbonyl)pyridine N-oxide,
5-amino-2-(6-cyano-2,2-dimethyl-2H-1-benzopyran-4-yl)pyridine N-oxide,
5-amino-2-(6-cyano-3,4-dihydro-2,2-dimethyl-2H-1-benzopyran-4-yl)pyridine N-oxide,
2-(6-cyano-2,2-dimethyl-2H-1-benzopyran-4-yl)-5-hydroxypyridine N-oxide,
5-chloro-2-(6-cyano-2,2-dimethyl-2H-1-benzopyran-4-yl)pyridine N-oxide,
5-chloro-2-(6-cyano-3,4-dihydro-2,2-dimethyl-2H-1-benzopyran-4-yl)pyridine N-oxide,
2-(6-cyano-2,2-dimethyl-2H-1-benzopyran-4-yl)-5-phenylpyridine N-oxide,
2-(6-acetyl-2,2-dimethyl-2H-1-benzopyran-4-yl)pyridine N-oxide,
2-(6-cyano-2,2-dimethyl-2H-1-benzopyran-4-yl)-5-methylpyridine N-oxide,
2-(6-cyano-3,4-dihydro-2,2-dimethyl-2H-1-benzopyran-4-yl)-5-methylpyridine N-oxide,
2-(6-bromo-2,2-dimethyl-2H-1-benzopyran-4-yl)pyridine N-oxide,
2-(6-cyano-2,2-dimethyl-2H-1-benzopyran-4-yl)-5-(4methylphenyl)pyridine N-oxide,
2-(6-acetyl-2-methyl-2-phenyl-2H-1-benzopyran-4-yl)pyridine N-oxide,
5-benzyloxy-2-(6-cyano-3,4-dihydro-2,2-dimethyl-2H-1-benzopyran-4-yl)pyridine N-oxide,
2-(6-cyano-3,4-dihydro-2,2-dimethyl-2H-1-benzopyran-4-yl)-5-hydroxypyridine N-oxide,
rac-trans-2-(6-cyano-3,4-dihydro-3-hydroxy-2,2-dimethyl-H-1-benzopyran-4-yl)pyridine N-oxide,
rac-cis-2-(6-cyano-3,4-dihydro-3-hydroxy-2,2-dimethyl-H-1-benzopyran-4-yl)pyridine N-oxide,
6-(6-cyano-3,4-dihydro-2,2-dimethyl-2H-1-benzopyran-4-yl)pyrimidine 1-oxide,
2-(6-cyano-3,4-dihydro-2,2-dimethyl-2H-1-benzopyran-4-yl)pyrazine 1-oxide,
4-(6-acetyl-2,2-dimethyl-2H-1-benzopyran-4-yl)-3-pyridinol,
4-(2,2-dimethyl-2H-1-benzopyran-4-yl)-3-pyridinol,
(−)-2-(6-cyano-3,4-dihydro-2,2-dimethyl-2H-1-benzopyran-4-yl)pyridine N-oxide and
(+)-2-(6-cyano-3,4-dihydro-2,2-dimethyl-2H-1-benzopyran-4-yl)pyridine N-oxide.

According to the process provided by the invention, the compounds of formula I and the pharmaceutically acceptable acid addition salts of those compounds which are basic are prepared as follows:

(a) for the preparation of a compound of formula I in which $R^6$ is an aryl or N-heteroaryl group carrying a hydroxy group in the 2-position, converting the lower alkoxy group in a compound of the formula

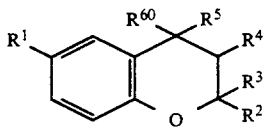

II wherein $R^1$, $R^2$, $R^3$, $R^4$ and $R^5$ are as described above and $R^{60}$ is an aryl or N-heteroaryl group carrying a lower alkoxy group in the 2-position, into a hydroxy group, or (b) for the preparation of a compound of formula I in which $R^6$ is a N-heteroaryl group carrying a N-oxide group in the 2-position, oxidizing a compound of the formula

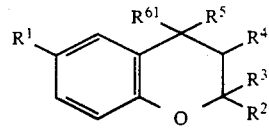

III wherein $R^1$, $R^2$, $R^3$, $R^4$ and $R^5$ are as described above and $R^{61}$ is a N-heteroaryl group having a nitrogen atom in the 2-position, or (c) for the preparation of a compound of formula I in which $R^6$ is a N-heteroaryl group carrying a hydroxy group in the 2position and having a nitrogen atom in the 3-position, reacting a compound of the formula

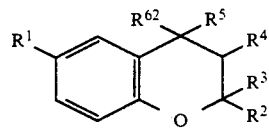

IV wherein $R^1$, $R^2$, $R^3$, $R^4$ and $R^5$ are as described above and $R^{62}$ is a N-heteroaryl group having a carbon atom in the 2-position and carrying a N-oxide group in the 3-position.

with a lower alkanoic acid anhydride and hydrolyzinq the product obtained, or (d) for the preparation of a compound of formula I in which $R^4$ and $R^5$ each is hydrogen and $R^6$ is a N-heteroaryl group carrying a N-oxide group in the 2-position, cyclizing a compound of the formula

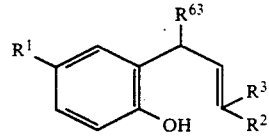

V wherein $R^1$, $R^2$ and $R^3$ are as described above and is a N-heteroaryl group carrying a N-oxide group in the 2-position, or (e) for the preparation of a compound of formula I in which $R^1$ is lower alkylsulphonyl, oxidizing a compound of formula I in which $R^1$ is lower alkylthio, or (f) for the preparation of a compound of formula I in which $R^1$ is lower alkanoyl or aroyl appropriately lower alkanoylating or aroylating a compound of formula I in which $R^1$ is hydrogen, or g) for the preparation of a compound of formula I in which $R^6$ is a 2-pyridyl N-oxide group carrying a lower alkoxy group in the o- or p-position to the N-oxide group, reacting a compound of formula I in which $R^6$ is a 2-pyridyl N-oxide group carrying a halogen atom in the o- or p-position to the N-oxide group with an alkali metal lower alkoxide at an elevated temperature, or h) for the preparation of a compound of formula I in which $R^4$ and $R^5$ each is hydrogen and $R^6$ is a hydroxy-substituted N-heteroaryl group carrying a N-oxide group in the 2-position, catalytically hydrogenating a compound of formula I in which $R^4$ and $R^5$ each is hydrogen and $R^6$ is a benzyloxy-substituted N-heteroaryl group carrying a N-oxide group in the 2-position, or i) for the preparation of a compound of formula I in which $R^4$ and $R^5$ together are a carbon-carbon bond and $R^6$ is a 3-hydroxy-4-pyridyl group, reacting a 3-[N,N-di(lower alkyl)carbamoyloxy]-pyridine with a compound of the formula

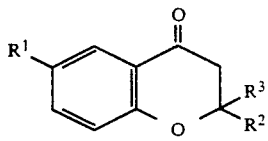

wherein $R^1$, $R^2$ and $R^3$ are as described above, in the presence of an alkali metal alkyl compound, and/or j) if desired, separating a mixture of diastereoisomeric racemates obtained into the diastereoisomeric racemates or optically pure diastereoisomers, and/or k) if desired, resolving a racemate obtained into the optical antipodes, and/or l) if desired, separating a cis/trans mixture obtained into the cis and trans isomers, and m) if desired, converting a basic compound of formula I obtained into a pharmaceutically acceptable acid addition salt.

The conversion of a lower alkoxy group, preferably methoxy, in a compound of formula II into a hydroxy group in accordance with embodiment (a) of the process can be carried out in a manner known per se. One convenient procedure comprises treating a compound of formula II with an alkali metal lower alkanethiolate (e.g. sodium methanethiolate), suitably in an inert organic solvent such as dimethylformamide and at an elevated temperature (e.g. about 100° C.). However, the conversion can also be carried out using other reagents such as lithium iodide, a tri(lower alkyl)silyl halide (e.g. trimethylsilyl iodide), boron tribromide or the like.

Known procedures can be used for the oxidation of a compound of formula III in accordance with embodiment (b) of the process. For example, a compound of formula III can be oxidized by treatment with hydrogen peroxide, an organic peracid such as peracetic acid, perbenzoic acid, m-chloroperbenzoic acid, perphthalic acid or the like, a perester, sodium metaperiodate, sodium perborate in acetic acid, etc. The oxidation is expediently carried out in an inert organic solvent such as a halogenated hydrocarbon (e.g. chloroform, dichloromethane, dichloroethane etc). When hydrogen peroxide is used as the oxidizing agent, the oxidation can also be carried out in acetic acid or the like. Conveniently, the oxidation is carried out at a temperature between about 0° C. and about 30° C., preferably at about room temperature.

Embodiment (c) of the process, namely the reaction of a compound of formula IV with a lower alkanoic acid anhydride and the subsequent hydrolysis of the resulting product, can be carried out according to methods known per se. For example, a compound of formula IV can be reacted with the anhydride, preferably acetic anhydride, at an elevated temperature, preferably at the reflux temperature of the reaction mixture. The product obtained, a compound corresponding to formula I in which $R^6$ is a N-heteroaryl group carrying a lower alkanoyloxy group in the 2-position and having a nitrogen atom in the 3-position, can then be hydrolyzed by treatment with an acid or a base in a known manner. The acid hydrolysis can be carried out using an aqueous mineral acid (e.g. hydrochloric acid, hydrobromic acid, sulphuric acid etc) or an organic acid (e.g. p-toluenesulphonic acid etc), conveniently in an inert organic solvent such as tetrahydrofuran, dioxan etc containing water and at about room temperature. The basic hydrolysis can be carried out using an alkali metal hydroxide such as sodium hydroxide or an alkali metal lower alkoxide (e.g. sodium methoxide, sodium ethoxide etc), conveniently in an inert organic solvent such as a lower alkanol (e.g. methanol, ethanol etc) at about room temperature.

The cyclization of a compound of formula V in accordance with embodiment (d) of the process can be conveniently carried out by treatment with an acid, suitably an inorganic acid such as sulphuric acid, and expediently in an inert organic solvent such as a halogenated hydrocarbon (e.g. dichloromethane, chloroform, dichloroethane etc). Suitably, this treatment is carried out at about room temperature. The cyclization takes place readily, and in certain circumstances it may be advisable or necessary to carry it out in situ.

The oxidation of a compound of formula I in which $R^1$ is lower alkylthio in accordance with embodiment (e) of the process can be carried out in accordance with known procedures. For example, the oxidation can be carried out by treatment with hydrogen peroxide, an organic peracid such as peracetic acid, perbenzoic acid, m-chloroperbenzoic acid, perphthalic acid or the like, a perester, sodium metaperiodate, sodium perborate in acetic acid, etc. The oxidation is expediently carried out in an inert organic solvent such as a halogenated hydrocarbon (e.g. chloroform, dichloromethane, dichloroethane etc). When hydrogen peroxide is used as the oxidizing agent, the oxidation can also be carried out in acetic acid or the like. Conveniently, the oxidation is carried out at a temperature between about 0° C. and about 30° C., preferably at about room temperature.

The lower alkanoylation or aroylation in accordance with embodiment (f) of the process can be carried out under the well-known conditions of a Friedel-Crafts reaction. Thus, for example, the compound of formula 1 in which $R^1$ is hydrogen can be reacted with an appropriate lower-alkanoyl halide (e.g. acetyl chloride) or aroyl halide (e.g. benzoyl chloride, 2-iodobenzoyl chloride, 4-nitrobenzoyl chloride etc) in the presence of a Lewis acid catalyst (e.g. aluminum chloride etc), suitably in an inert organic solvent (e.g. nitromethane). Conveniently, the reaction is carried out at a temperature between about 0° C. and room temperature, although it can be carried out at a higher temperature where required.

The replacement of a halogen atom by a lower alkoxy group in accordance with embodiment (g) of the process can be carried out in a manner known per se. The reaction of the respective compound of formula I, preferably one in which the halogen atom is a chlorine atom, with an alkali metal lower alkoxide (e.g. sodium methoxide, sodium ethoxide etc) is conveniently carried out in an inert organic solvent, preferably the lower alkanol corresponding to the alkali metal lower alkoxide which is used. The reaction is preferably carried out at the reflux temperature of the reaction mixture and under an inert atmosphere (e.g. nitrogen).

The catalytic hydrogenation in accordance with embodiment (h) of the process can be carried out in a known manner. The catalytic hydrogenation is conveniently carried out in an inert organic solvent such as a lower alkanol (e.g. methanol) using a noble metal catalyst such as a palladium or platinum catalyst which may be supported on a suitable carrier material (e.g. palladium-on-carbon). The catalytic hydrogenation is expediently carried out at about room temperature and under atmospheric pressure.

The reaction in accordance with embodiment (i) of the process is conveniently carried out by firstly treating a 3-[N,N-di(lower alkyl)carbamoyloxy]-pyridine, especially 3-(N,N-diethylcarbamoyloxy)-pyridine, with an alkali metal alkyl compound, especially n-butyllithium, and subsequently adding a compound of formula VI. The reaction is conveniently carried out in an inert organic solvent or solvent mixture such as an aliphatic hydrocarbon (e.g. hexane) or a cyclic ether (e.g. tetrahydrofuran) or a mixture thereof. The reaction is suitably carried out at a temperature between about −78° C. and room temperature.

The separation of a mixture of diastereoisomeric racemates in accordance with embodiment (j) of the process, the resolution of a racemate in accordance with embodiment (k) of the process and the separation of a cis/trans mixture in accordance with embodiment (l) of the process can be carried out according to methods known per se; for example, by chromatography using a suitable solvent system, whereby in the case of the resolution of a racemate the chromatographic medium must be chiral (e.g. β-cyclodextrin bonded to silica). Further, an acidic racemate can be resolved using a chiral base (e.g. quinine) and a basic racemate can be resolved using a chiral acid (e.g. camphorsulphonic acid). A further procedure for the separation of diastereoisomers and of cis/trans isomers involves crystallization from a suitable solvent system.

In accordance with embodiment (m) of the process a basic compound of formula I (i.e. one in which $R^6$ is a N-heteroaryl group carrying at least one amino substituent) is converted into a pharmaceutically acceptable acid addition salt. This can be effected by treating a basic compound of formula I with an inorganic acid such as a hydrohalic acid (e.g. hydrochloric acid, hydrobromic acid or hydroiodic acid), sulphuric acid, phosphoric acid, nitric acid etc or an organic acid such as acetic acid, maleic acid, fumaric acid, tartaric acid, citric acid, salicylic acid, methanesulphonic acid, p-toluenesulphonic acid etc.

The starting materials of formulae II, III and IV hereinbefore are novel and also form objects of the invention. Those starting materials of formulae II, III and IV in which $R^4$ and $R^5$ each is hydrogen or $R^4$ and $R^5$ together are a carbon-carbon bond can be prepared in accordance with Reaction Scheme I hereinafter in which $R^2$, $R^3$ and $R^{62}$ are as described above, $R^7$ is a lower alkoxy group, is hydrogen, halogen, trifluoromethyl, nitro, cyano, lower alkyl, lower alkylthio or lower alkylsulphonyl and is an aryl or N-heteroaryl group carrying a lower alkoxy group in the 2-position, a N-heteroaryl group having a nitrogen atom in the 2-position or a N-heteroaryl group having a carbon atom in the 2-position and a nitrogen atom in the 3-position. It will be appreciated that, in this Reaction Scheme, the compounds of formulae X and XI in which $R^{64}$ is an aryl or N-heteroaryl group carrying a lower alkoxy group in the 2-position correspond to startinq materials of formula II in which $R^4$ and $R^5$ each is hydrogen or $R^4$ and $R^5$ together are a carbon-carbon bond and that the compounds of formulae X and XI in which $R^{64}$ is a N-heteroaryl group having a nitrogen atom in the 2-position correspond to starting materials of formula III in which $R^4$ and $R^5$ each is hydrogen or $R^4$ and $R^5$ together are a carbon-carbon bond.

Reaction Scheme I

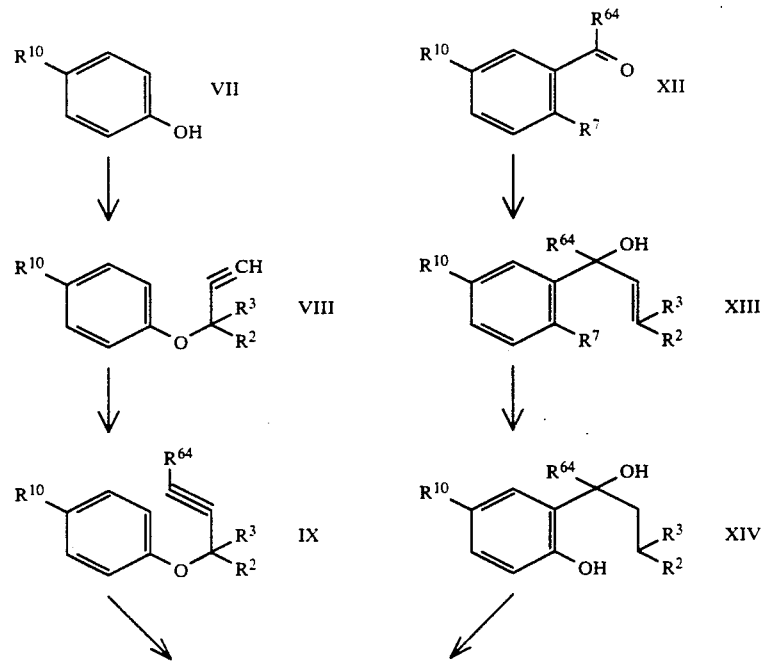

Reaction Scheme 1 -continued

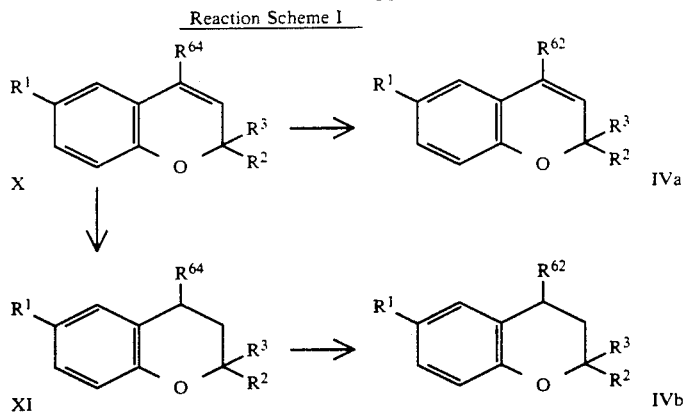

In connection with Reaction Scheme I, a compound of formula VII, which is a known compound or an analogue of a known compound, is reacted with a compound of the formula X—C(R$^2$)(R$^3$)—C≡CH, wherein X is chlorine, bromine or hydroxy, to give a compound of formula VIII. This reaction can be carried out in a known manner. For example, when X is chlorine or bromine the reaction can be carried out in a mixture of an inert organic solvent such as a halogenated aliphatic hydrocarbon (e.g. dichloromethane) and water in the presence of a base such as an alkali metal hydroxide (e.g. sodium hydroxide or potassium hydroxide) and a phase transfer catalyst such as benzyltrimethylammonium hydroxide, conveniently at about room temperature. Again, for example, when X is hydroxy the reaction can be carried out in an inert organic solvent such as a halogenated aliphatic hydrocarbon (e.g. dichloromethane) in the presence of a condensation agent such as diethyl azodicarboxylate/triphenylphosphine, conveniently at about room temperature.

A compound of formula VIII is subsequently reacted with a compound of the formula X$^1$—R$^{64}$, wherein R$^{64}$ is as described above and X$^1$ is bromine or iodine, in the presence of copper(I) iodide, a triarylphosphine (e.g. triphenylphosphine) and palladium(II) chloride to give a compound of formula IX. This reaction is conveniently carried out in the presence of a di(lower alkyl)amine such as diethylamine or a tri(lower alkyl)amine such as triethylamine and at about room temperature. In certain circumstances it may be advisable or even necessary to carry out this reaction under an inert gas atmosphere (e.g. nitrogen).

A compound of formula IX is then converted into a compound of formula X in which R$^1$ is hydrogen, halogen, trifluoromethyl, nitro, cyano, lower alkyl, lower alkylthio or lower alkylsulphonyl by heating, conveniently in an inert organic solvent such as a halogenated aromatic hydrocarbon (e.g. chlorobenzene, 1,2-dichlorobenzene etc) and preferably at the reflux temperature of the mixture.

A compound of formula X in which R$^1$ is hydrogen, halogen, trifluoromethyl, nitro, cyano, lower alkyl, lower alkylthio or lower alkylsulphonyl can also be prepared by firstly reacting a compound of formula XII, which is a known compound or an analogue of a known compound, with a compound of the formula (R$^2$)(R$^3$)C=CH—MgX, wherein R$^2$, R$^3$ and X are as described above, under the conventionally used conditions of a Grignard reaction to give a compound of formula XIII.

The lower alkoxy group R$^7$ in a compound of formula XIII obtained is then converted into a hydroxy group to give a compound of formula XIV. This conversion can be carried out by treating a compound of formula XIII with an alkali metal lower alkanethiolate (e.g. sodium methanethiolate), suitably in an inert organic solvent such as dimethylformamide and at an elevated temperature (e.g. about 100° C.). However, the conversion can also be carried out using other reagents such as lithium iodide, a tri(lower alkyl)silyl halide (e.g. trimethylsilyl iodide), boron tribromide or the like. It will be appreciated that when R$^{64}$ in the compound of formula XIII is an aryl or N-heteroaryl group carrying a lower alkoxy group in the 2-position, this group may be partially converted into a hydroxy group during this conversion.

A thus-obtained compound of formula XIV is then converted into a compound of formula X by heating, conveniently in a high-boiling aliphatic ether such as diethyleneglycol dimethylether or the like.

A compound of formula X obtained in which R$^1$ is hydrogen can be converted into a compound of formula X in which R$^1$ is halogen, nitro, lower alkanoyl, aroyl or tertiary lower alkyl according to methods known per se. For example, a compound of formula X in which R$^1$ is hydrogen can be chlorinated or brominated by treatment with elemental chlorine or bromine, conveniently in an inert organic solvent such as a halogenated hydrocarbon (e.g. dichloromethane, chloroform, carbon tetrachloride etc) and in the presence of a base (e.g. a tertiary amine such as triethylamine or pyridine). Again, for example, a compound of formula X in which R$^1$ is hydrogen can be nitrated by treatment with nitronium tetrafluoroborate, suitably in an inert organic solvent such as acetonitrile. Yet again, for example, a compound of formula X in which R$^1$ is hydrogen can be lower alkanoylated or aroylated by treatment with a lower alkanoyl halide such as acetyl chloride or an aroyl halide such as benzoyl chloride in the presence of a catalyst such as aluminum chloride or the like. Further, for example, a compound of formula I in which R$^1$ is hydrogen can be converted into a compound of formula I in which R$^1$ is tertiary lower alkyl by reaction with a tertiary alkanoyl halide (e.g. pivaloyl chloride) in the presence of a catalyst such as aluminum chloride or the like. A compound of formula X in which R$^1$ is cyano can be converted into a compound of formula X in which R$^1$ is carboxy in a known manner, for example by heating with an aqueous alkali metal hydroxide solution such as aqueous sodium hydroxide solution, and the resulting compound of formula X in which R$^1$ is carboxy can be converted into a compound of formula X in which $R^1$ is lower alkoxycarbonyl, carbamoyl, mono(lower alkyl)carbamoyl or di(lower alkyl)carbamoyl according to methods known per se; for example, by transformation into the corresponding carboxylic acid halide (e.g. chloride) using an appropriate halogenating agent (e.g. thionyl chloride) and reacting the halide with, respectively, an appropriate lower alkanol or ammonia, a lower alkylamine (e.g. methylamine, ethylamine etc) or a di(lower alkyl)amine (e.g. dimethylamine, diethylamine etc).

A compound of formula X in which $R^1$ is hydrogen, halogen, trifluoromethyl, cyano, lower alkyl, lower alkylthio or lower alkylsulphonyl can be converted into a compound of formula XI in which $R^1$ is hydrogen, halogen, trifluoromethyl, cyano, lower alkyl, lower alkylthio or lower alkylsulphonyl by hydrogenation in the presence of a noble metal catalyst (e.g. a palladium or platinum catalyst) in a manner known per se; for example, in an inert organic solvent such as a lower alkanol (e.g. methanol, ethanol) etc at about room temperature and under atmospheric pressure.

A compound of formula XI in which $R^1$ is hydrogen can be converted into a compound of formula XI in which $R^1$ is halogen, nitro, lower alkanoyl, aroyl or tertiary lower alkyl in a manner analogous to that described earlier in connection with the conversion of a compound of formula X in which $R^1$ is hydrogen into a compound of formula X in which $R^1$ is halogen, nitro, lower alkanoyl, aroyl or tertiary lower alkyl. Further, a compound of formula XI in which $R^1$ is cyano can be converted into a compound of formula XI in which $R^1$ is carboxy and the latter compound can be converted into a compound of formula XI in which $R^1$ is lower alkoxycarbonyl, carbamoyl, mono(lower alkyl)carbamoyl or di(lower alkyl)carbamoyl, likewise as described earlier in connection with corresponding compounds of formula X. A compound of formula XI in which $R^1$ is carbamoyl can be converted into a compound of formula I in which $R^1$ is cyano in a manner known per se; for example, by dehydration using phosphorus oxychloride.

Certain substituents present on an aforementioned N-heteroaryl group denoted by $R^{64}$ in compounds of formulae X and XI can be functionally modified to give other substituents, i.e. an interconversion of substituents can be effected. For example, a benzyloxycarbonyl-substituted N-heteroaryl group can be debenzylated to give a carboxy-substituted N-heteroaryl group (e.g. by heating with palladium-on-charcoal and formic acid) and the latter can be esterified with a diazoalkane to give a lower alkoxycarbonyl-substituted N-heteroaryl group. Further, a nitro-substituted N-heteroaryl group in a compound of formula X can be reduced to an amino-substituted N-heteroaryl group using a reducing system such as iron powder/acetic acid, whereby the double bond in the 3,4-position of the molecule is not affected. Of course, when a compound of formula X in which $R^{64}$ is a nitro-substituted N-heteroaryl group is catalytically hydrogenated, not only is the nitro-substituted N-heteroaryl group converted into an amino-substituted N-heteroaryl group, but also the double bond in the 3,4-position of the molecule is reduced to a single bond. Other functional modifications which can be carried out include the conversion of an amino-substituted N-heteroaryl group into a hydroxy-substituted or chlorosubstituted N-heteroaryl group and the conversion of an amino-substituted N-heteroaryl group into an iodosubstituted N-heteroaryl group and the conversion of the latter into a (lower alkyl)phenyl-substituted N-heteroaryl group; whereby these functional modifications can be carried out according to methods known per se.

Where a starting material of formula IV is required, a compound of formula X or XI in which $R^{64}$ is a N-heteroaryl group having a carbon atom in the 2-position and a nitrogen atom in the 3-position is oxidized. This oxidation can be carried out according to known procedures. For example, a compound of formula X or XI can be oxidized by treatment with hydrogen peroxide, an organic peracid such as peracetic acid, perbenzoic acid, m-chloroperbenzoic acid, perphthalic acid or the like, a perester, sodium metaperiodate, sodium perborate in acetic acid, etc. The oxidation is expediently carried out in an inert organic solvent such as a halogenated hydrocarbon (e.g. chloroform, dichloromethane, dichloroethane etc). When hydrogen peroxide is used as the oxidizing agent, the oxidation can also be carried out in acetic acid or the like. Conveniently, the oxidation is carried out at a temperature between about 0° C. and about 30° C., preferably at about room temperature.

A further method for the preparation of starting materials of formula III in which $R^4$ and $R^5$ each is hydrogen and $R^{61}$ is a N-heteroaryl group having a nitrogen atom in the 2-position and a chlorine atom in the o- or p-position to said nitrogen atom comprises treating a compound of formula I in which $R^4$ and $R^5$ each is hydrogen and $R^6$ is a N-heteroaryl group carrying a N-oxide group in the 2-position with phosphorus oxychloride at an elevated temperature (e.g about 80° C.). The treatment yields a mixture of the aforementioned o-chloro and p-chloro compounds and this mixture can be separated into the individual compounds by chromatography.

Yet a further method for the preparation of starting materials of formula III in which $R^4$ and $R^5$ together are a carbon-carbon bond comprises treating a compound of formula I in which $R^4$ and $R^5$ each is hydrogen and $R^6$ is a N-heteroaryl group carrying a N-oxide group in the 2-position with a lower alkanoic acid anhydride, especially acetic anhydride, at an elevated temperature (e.g. about 120° C.).

The starting materials of formulae II, III and IV in which $R^4$ is hydroxy and $R^5$ is hydrogen can be prepared by firstly converting a compound of formula II, III or IV in which $R^4$ and $R^5$ together are a carbon-carbon bond into the corresponding 3,4-epoxide in a manner known per se. For example, this epoxidation can be carried out in an inert organic solvent or solvent mixture such as a lower alkanol (e.g. methanol), acetonitrile or a mixture thereof using hydrogen peroxide in the presence of an alkali metal tungstate (e.g. sodium tungstate) at an elevated temperature (e.g. about 50° C.). Subsequently, the 3,4-epoxide is converted into the desired starting material in which $R^4$ is hydroxy and $R^5$ is hydrogen by catalytic hydrogenation in a manner known per se; for example, in an inert organic solvent such as a lower alkanol (e.g. ethanol) and in the presence of a noble metal catalyst such as a platinum or palladium catalyst which may be supported on a suitable carrier material (e.g. palladium-on-carbon). Suitably, the catalytic hydrogenation is carried out at about room temperature and under atmospheric pressure.

As in the case of the compounds of formula I, depending on the values for $R^2$ and $R^3$ and for $R^4$ and $R^5$ in the starting materials of formulae II, III and IV these starting materials can be present as optical isomers, racemates, diastereoisomers and cis/trans isomers The separation of a mixture of diastereoisomeric racemates, the resolution of a racemate and the separation of a cis/trans mixture can be effected as described earlier in connection with the compounds of formula I. A particular procedure for the resolution of a racemic compound of formula XI hereinbefore in which $R^1$ is carboxy comprises treating such a compound with an appropriate chiral base such as quinine, separating the optically active salts by fractional crystallization and liberating the optically active compound from the salt by treatment with an appropriate acid.

The starting materials of formula V hereinbefore are novel and also form an object of the present invention. They can be prepared in accordance with Reaction Scheme II hereinafter in which $R^1$, $R^2$, $R^3$ and $R^{63}$ are as described above; $R^8$ is lower alkyl and $R^9$ is lower alkylsulphonyl or arylsulphonyl.

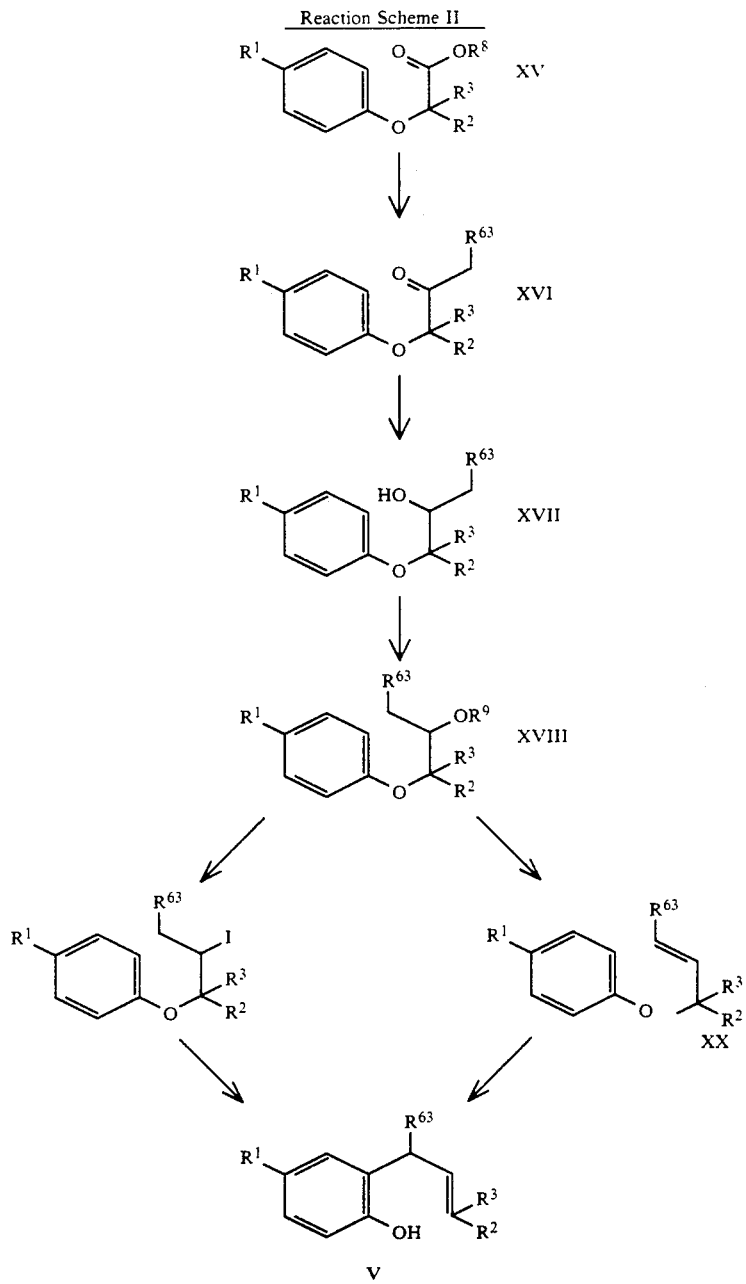

In connection with Reaction Scheme II, a compound of formula XV, which is a known compound or an analogue of a known compound, is converted into a compound of formula XVI by reaction with a N-heterocyclic N-oxide carrying a methyl group in the 2-position (e.g. 2-picoline N-oxide) in the presence of a strong base, preferably an alkali metal hydride such as sodium hydride or an alkali metal di(lower alkyl)amide such as lithium diethylamide. Conveniently, this reaction is carried out in an inert organic solvent such as a cyclic ether (e.g. tetrahydrofuran) at the reflux temperature of the reaction mixture or at about −78° C. to about room temperature when a di(lower alkyl)amide is used as the strong base.

A compound of formula XVI is then reduced in a manner known per se to give a compound of formula XVII. For example, the reduction can be conveniently carried out using a complex metal hydride such as an alkali metal borohydride (e.g. sodium borohydride) in a suitable inert organic solvent (e.g. an alcohol such as ethanol), conveniently at about room temperature.

The subsequent conversion of a compound of formula XVII into a compound of formula XVIII can be carried out according to known methods; for example, by reaction with a lower alkanesulphonyl halide (e.g. methanesulphonyl chloride etc) or an aromatic sulphonyl halide (e.g. benzenesulphonyl chloride, p-toluenesulphonyl chloride etc) in an inert organic solvent and in the presence of an acid-binding agent such as a tertiary amine (e.g. triethylamine, pyridine etc). An excess of such an amine can be used and can simultaneously serve as the solvent. Suitably, this reaction is carried out at about room temperature.

In the next step the group $OR^9$ in a compound of formula XVIII is replaced by an iodine atom in a known manner to give a compound of formula XIX. This step can be carried out, for example, by treatment with an alkali metal iodide such as sodium iodide in acetone at an elevated temperature, suitably at the reflux temperature of the reaction mixture.

The iodine atom in a compound of formula XIX is then eliminated and the product is subjected to a Claisen rearrangement to give a desired starting material of formula V. The elimination and rearrangement are carried out in one step by heating a compound of formula XIX with a suitable tertiary amine (e.g. diisopropylethylamine etc), conveniently at the reflux temperature, in an inert organic solvent such as a lower alkanol (e.g. methanol, ethanol etc).

An alternative route from a compound of formula XVIII comprises eliminating therefrom the group $OR^9$ by treatment with a strong base such as an alkali metal hydride (e.g. sodium hydride), conveniently in an organic solvent such as a lower alkanol (e.g. isopropanol) and at about room temperature, to give a compound of formula XX.

A resulting compound of formula XX is then subjected to a Claisen rearrangement to give a desired starting material of formula V. This is conveniently carried out by heating in a high-boiling organic solvent such as a halogenated aromatic hydrocarbon (e.g. chlorobenzene, 1,2-dichlorobenzene etc).

The starting materials used in embodiment (i) of the process, namely the 3-[N,N-di(lower alkyl)carbamoyloxy]pyridines and the compounds of formula VI, are known compounds or analogues of known compounds which can be prepared in a similar manner to the known compounds.

The compounds of formula I and their aforementioned salts possess a pronounced potassium channel activating activity and can be used as medicaments, especially in the control or prevention of hypertension, congestive heart failure, angina pectoris, peripheral and cerebral vascular disease and smooth muscle disorders (e.g. of the gastrointestinal, respiratory, uterine and urinary tracts as in peptic ulcers, irritable bowel syndrome, diverticular disease, reversible airways obstruction, asthma, premature labour and incontinence). Furthermore, they may also be used for the restoration of hair loss.

The potassium channel activating activity of the compounds of the present invention can be demonstrated in the test described hereinafter:

Hepatic portal veins are removed from male Sprague-Dawley rats and suspended in organ baths under an initial tension of 0.5 g for the isometric recording of tension. The veins are incubated in Krebs solution (consisting of 118 mM of sodium chloride, 25 mM of sodium hydrogen carbonate, 10.5 mM of D-glucose, 4.7 mM of potassium chloride, 0.4 mM of magnesium sulphate, 1.2 mM of potassium dihydrogen phosphate and 2.5 mM of calcium chloride) which is gassed with 95% oxygen and 5% carbon dioxide and maintained at 37° C. After incubation for 0.5 hour to 1 hour a further 20 mmol of potassium chloride is added followed after 0.25 hour to 0.5 hour by increasing concentrations of the test substance. The activity of the test substance is expressed as the $IC_{50}$ value, which is the concentration of test substance producing a half-maximal reduction of the contractions caused by the potassium chloride.

TABLE

| Compound | $IC_{50}$ (μmol) |
| --- | --- |
| A | 0.16 ± 0.02 |
| B | 0.038 ± 0.002 |
| C | 0.014 ± 0.001 |
| D | 0.56 ± 0.07 |
| E | 0.015 ± 0.0005 |
| F | 0.28 ± 0.03 |
| G | 0.019 ± 0.0012 |
| H | 3.1 ± 0.8 |

Compound A: 2-(6-Cyano-3,4-dihydro-2,2-dimethyl-2H-1-benzopyran-4-yl)pyridine N-oxide.
Compound B: 2-(6-Cyano-2,2-dimethyl-2H-1-benzopyran-4-yl)pyridine N-oxide.
Compound C: 2-(3,4-Dihydro-2,2-dimethyl-6-nitro-2H-1-benzopyran-4-yl)pyridine N-oxide.
Compound D: 2-(6-Acetyl-3,4-dihydro-2,2-dimethyl-2H-1-benzopyran-4-yl)pyridine N-oxide.
Compound E: 2-(6-Cyano-2,2-dimethyl-2H-1-benzopyran-4-yl)-5-phenylpyridine N-oxide.
Compound F: rac-trans-2-(6-cyano-3,4-dihydro-3-hydroxy-2,2-dimethyl-2H-1-benzopyran-4-yl)pyridine N-oxide.
Compound G: 2-(6-Cyano-2-ethyl-2-methyl-2H-1-benzo-pyran-4-yl)pyridine N-oxide.
Compound H: 4-(5-Cyano-2-hydroxyphenyl)-2,2-dimethyl-2H-1-benzopyran-6-carbonitrile.

The compounds of formula I and their aforementioned salts can be used as medicaments, for example in the form of pharmaceutical preparations. The pharmaceutical preparations can be administered orally, for example in the form of tablets, coated tablets, dragees, hard and soft gelatine capsules, solutions, emulsions or suspensions. They can, however, also be administered rectally, for example in the form of suppositories, or parenterally, for example in the form of injection solutions.

For the manufacture of pharmaceutical preparations the compounds of formula I and their aforementioned salts can be processed with pharmaceutically inert inorganic or organic excipients. Suitable excipients which can be used for tablets, coated tablets, dragees and hard gelatine capsules are, for example, lactose, maize starch or derivatives thereof, talc, stearic acid or its salts etc. Suitable excipients for soft gelatine capsules are, for example, vegetable oils, waxes, fats, semi-solid and liquid polyols etc. Water, polyols, saccharose, invert sugar, glucose etc are examples of suitable excipients for the manufacture of solutions and syrups. Suitable excipients for injection solutions are, for example, water, alcohols, polyols, glycerine, vegetable oils etc. Natural or hardened oils, waxes, fats, semi-liquid or liquid polyols etc are examples of suitable excipients for suppositories.

The pharmaceutical preparations can also contain preserving agents, solubilizing agents, stabilizing agents, wetting agents, emulsifying agents, sweetening agents, colouring agents, flavouring agents, salt for varying the osmotic pressure, buffers, coating agents or antioxidants. They can also contain other therapeutically valuable substances.

In accordance with the invention the compounds of formula I and their aforementioned salts can be used in the control or prevention of illnesses, especially in the control or prevention of hypertension, congestive heart failure, angina pectoris, peripheral and cerebral vascular disease and smooth muscle disorders. The dosage of the compounds of formula I and their aforementioned salts can vary within wide limits and will, of course, be adjusted to the individual requirements in each particular case. In general, in the case of oral administration to adults, a daily dosage of about 0.1 mg to about 10 mg, preferably about 0.2 mg to about 5 mg should be appropriate, although the upper limit mentioned can be exceeded when this is shown to be expedient. The daily dosage can be administered as a single dosage or in divided doses.

The following Examples illustrate the present invention:

EXAMPLE 1

130 mg of 3,4-dihydro-2,2-dimethyl-4-(2-pyridyl)-2H-1-benzopyran were dissolved in 10 ml of dichloromethane at room temperature and 93 mg of m-chloroperbenzoic acid were added. After 2 hours thin-layer chromatography indicated that some starting material was still present, whereupon further m-chloroperbenzoic acid was added until the reaction was complete. The mixture was washed in succession with sodium bisulphite solution, sodium bicarbonate solution and water, dried over sodium sulphate and evaporated to give 105 mg of 2-(3,4-dihydro-2,2-dimethyl-2H-1-benzopyran-4-yl)pyridine N-oxide in the form of an oil. NMR (300 MHz, CDCl$_3$): 8.36-8.30 (1H, m) 7.21-7.04 (4H, m), 6.89-6.76 (3H, m), 5.36-5.25 (1H, m), 2.46 (1H, dd, 14Hz, 6.5Hz), 1.75 (1H, broad t, 14Hz), 1.44 (3H, s), 1.40 (3H, s). MS (EI): 255 (M+, 238 (M+—OH).

The 3,4-dihydro-2,2-dimethyl-4-(2-pyridyl)-2H-1-benzopyran used as the starting material was prepared as follows:

(A) 43.84 g of 1-bromo-2-methylprop-1-ene in 150 ml of tetrahydrofuran were added dropwise to 9.8 g of magnesium in 50 ml of tetrahydrofuran while heating at reflux. After 1 hour the mixture was allowed to cool to room temperature, whereupon 47.7 g of 2-methoxyphenyl 2-pyridyl ketone in 200 ml of tetrahydrofuran were added slowly. After stirring for 2 hours at room temperature 200 ml of saturated ammonium chloride were added and the mixture was extracted with ethyl acetate. The organic extract was dried over sodium sulphate and evaporated. The residue was chromatographed on silica gel using ethyl acetate/petroleum ether (1:6) followed by ethyl acetate/petroleum ethyl (1:4) for the elution to yield 36.6 g of 1-(2-methoxyphenyl)-3-methyl-1-(2-pyridyl)-2-buten-1-ol in the form of an oil.

(B) 36.6 g of 1-(2-methoxyphenyl)-3-methyl-1-(2-pyridyl)- 2-buten-1-ol were heated at 70° C. in 200 ml of dimethylformamide with 28.6 g of sodium methanethiolate. After 10 hours the mixture was allowed to cool to room temperature, poured into dilute hydrochloric acid and extracted with ethyl acetate. The organic extract was dried over sodium sulphate and evaporated. The residue was chromatographed on silica gel using ethyl acetate for the elution to give 28.5 g of 1-(2-hydroxyphenyl)-3-methyl-1(2-pyridyl)-2-buten-1-ol in the form of an oil.

(C) 4.42 g of 1-(2-hydroxyphenyl)-3-methyl-1-(2-pyridyl)-2-buten-1-ol were dissolved in 70 ml of diethylene glycol dimethyl ether and heated at 150° C. for 2 hours. The mixture was allowed to cool to room temperature, the solvent was removed by evaporation and the residue was partitioned between ethyl acetate and sodium chloride solution. The organic phase was dried over sodium sulphate and evaporated. The residue was chromatographed on silica gel using ethyl acetate/petroleum ether (1:4) for the elution to give 2.4 g of 2,2-dimethyl-4-(2-pyridyl)-2H-1-benzopyran of melting point 80°-82° C.

(D) 6.95 g of 2,2-dimethyl-4-(2-pyridyl)-2H-1-benzopyran were dissolved in 100 ml of ethanol and shaken at room temperature with 10% palladium-on-charcoal under a hydrogen atmosphere. After the required volume of hydrogen had been taken up the catalyst was filtered off, the filtrate was evaporated and the residue was recrystallized from n-hexane to give 5.07 g of 3,4-dihydro-2,2-dimethyl-4-(2-pyridyl)-2H-1-benzopyran of melting point 99°-101° C.

EXAMPLE 2

245 mg of 3,4-dihydro-2,2-dimethyl--nitro-4-(2-pyridyl)-2H-1-benzopyran were dissolved in 5 ml of dichloromethane at room temperature and 149 mg of m-chloroperbenzoic acid were added. After stirring at room temperature for 3 days further m-chloroperbenzoic acid was added until starting material could no longer be detected by thin-layer chromatography. The mixture was washed in succession with sodium bisulphite solution, sodium bicarbonate solution and sodium chloride solution, dried over sodium sulphate and evaporated. The residue was chromatographed on silica gel using 4% (v/v) ethanol/dichloromethane for the elution and the resulting foam was triturated with n-hexane to give 80 mg of 2-(3,4-dihydro-2,2-dimethyl-6-nitro-2H-1-benzopyran-4-yl)pyridine N-oxide of melting point 116°-119° C.

The 3,4-dihydro-2,2-dimethyl-6 -nitro-4-(2-pyridyl)-2H-1-benzopyran used at the starting material was prepared as follows:

1.32 g of 3,4-dihydro-2,2-dimethyl-4-(2-pyridyl)-2H-1-benzopyran were dissolved in 20 ml of acetonitrile and 0.73 g of nitronium tetrafluoroborate was added at room temperature. After 1 hour the mixture was poured into water and extracted with ethyl acetate. The organic extract was washed with sodium chloride solution, dried over sodium sulphate and evaporated to give an oil. This oil was chromatographed on silica gel using ethyl acetate/petroleum ether (1:4) for the elution. 245 mg of 3,4-dihydro-2,2-dimethyl-6 -nitro-4-(2-pyridyl)-2H-1-benzopyran were obtained in the form of an oil.

EXAMPLE 3

261 mg of 6-acetyl-3,4-dihydro-2,2 -dimethyl-4-(2-pyridyl)-2H-1-benzopyran were dissolved in 20 ml of dichloromethane at room temperature and 250 mg of m-chloroperbenzoic acid were added. After stirring at room temperature for 3 days the mixture was washed in succession with sodium bisulphite solution, sodium bicarbonate solution and water, dried over sodium sulphate and evaporated. The residue was chromatographed on silica gel using 2%-5% (v/v) methanol/chloroform for the elution. The resulting foam was triturated with methylcyclohexane and the solid obtained was recrystallized from t-butyl methyl ether to give 20 mg of 2-(6-acetyl-3,4-dihydro-2,2-dimethyl-2H-1-benzopyran-4-yl)pyridine N-oxide of melting point 132°-133° C.

The 6-acetyl-3,4-dihydro-2,2-dimethyl-4-(2-pyridyl)-2H-1-benzopyran used as the starting material was prepared as follows:

1.56 g of 3,4-dihydro-2,2-dimethyl-2H-1-benzopyran-4-yl)pyridine were dissolved in 20 ml of nitromethane at room temperature. 1.67 g of aluminum chloride and 1.11 g of acetyl chloride were added and the mixture was stirred at 50° C. for 1 hour. Dilute sodium hydroxide solution was added and the mixture was extracted with ethyl acetate. The organic extract was washed with sodium chloride solution, dried over sodium sulphate and evaporated. The residue was chromatographed on silica gel using ethyl acetate/petroleum ether (1:2) and then ethyl acetate/petroleum ether (1:1) for the elution. The residue was triturated with n-hexane to give a solid which, after recrystallization from t-butyl methyl ether, gave 261 mg of 6-acetyl-3,4-dihydro-2,2-dimethyl-4-(2-pyridyl)-2H-1benzopyran of melting point 102°-105° C.

EXAMPLE 4

101 mg of 6-acetyl-3,4-dihydro-2,2-dimethyl-4-(3-methyl-2-pyridyl)-2H-1-benzopyran were dissolved in 5 ml of dichloromethane at room temperature and 91 mg of m-chloroperbenzoic acid were added. After 1 hour the mixture was washed in succession with sodium bisulphite solution, sodium bicarbonate solution and water. The organic extract was dried over sodium sulphate and evaporated to give an oil. This oil was triturated with t-butyl methyl ether to give a solid which, after recrystallization from ethyl acetate/t-butyl methyl ether, gave 28 mg of 2-(6-acetyl-3,4-dihydro-2,2-dimethyl-2H-1-benzopyran-4-yl)-3-methylpyridine N-oxide of melting point 154°-156° C.

The 6-acetyl-3,4-dihydro-2,2-dimethyl-4-(3-methyl-2-pyridyl)-2H-1-benzopyran used as the starting material was prepared as follows:

(A) 35.5 g of o-bromoanisole were added dropwise to 5.71 g of magnesium turnings covered with 50 ml of tetrahydrofuran while heating to maintain reflux. 15 minutes after completion of the addition 14.93 g of 2-cyano-3-methylpyridine in 150 ml of tetrahydrofuran were added dropwise without further heating. After 1 hour at room temperature dilute hydrochloric acid and ethyl acetate were added followed by dilute sodium hydroxide solution to pH 14. The mixture was extracted with ethyl acetate, the organic extract was dried over sodium sulphate and then evaporated. The residue was chromatographed on silica gel using ethyl acetate/petroleum ether (1:3) and then ethyl acetate/petroleum ether (1:2) for the elution. There were obtained 9.81 g of 2-methoxyphenyl 3-methyl-2-pyridyl ketone in the form of a solid of melting point 98°-100° C.

(B) 9.23 g of 1-bromo-2-methylprop-1-ene were added dropwise to 2.5 g of magnesium turnings covered with tetrahydrofuran while heating. 7.76 g of 2-methoxyphenyl 3-methyl-2-pyridyl ketone were added while heating to reflux. After 4 hours the mixture was allowed to cool to room temperature. Saturated ammonium chloride solution was added and the resulting mixture was extracted with diethyl ether. The organic extract was dried over sodium sulphate and evaporated. The residue was chromatographed on silica gel using ethyl acetate/petroleum ether (1:4) for the elution. There were obtained 5.75 g of 1-(2-methoxyphenyl)-3-methyl-1-(3-methyl-2-pyridyl)-2-buten-1-ol in the form of an oil.

(C) 7.13 g of 1-(2-methoxyphenyl)-3-methyl-1-(3-methyl-2-pyridyl)-2-buten-1-ol were dissolved in 100 ml of dimethylformamide at room temperature and 5.29 g of sodium methanethiolate were added. After stirring at 120° C. for 2 hours the mixture was allowed to cool to room temperature and then evaporated. Water and ethyl acetate were added, and the organic phase was separated, dried over sodium sulphate and evaporated. The residue was chromatographed on silica gel using ethyl acetate/petroleum ether (1:4) for the elution. There were obtained 4.53 g of 1-(2-hydroxyphenyl)-4-methyl-1-(3-methyl-2-pyridyl)-2-buten-1-ol in the form of an oil.

(D) 4.5 g of 1-(2-hydroxyphenyl)-3-methyl-1-(3-methyl-2-pyridyl)-2-buten-1-ol were dissolved in 50 ml of diethylene glycol dimethyl ether and heated at reflux for 1 hour. The mixture was allowed to cool to room temperature and then evaporated. The residue was chromatographed on silica gel using ethyl acetate/petroleum ether (1:4) and then ethyl acetate/petroleum ether (1:2) for the elution to give 2.97 g of 2,2-dimethyl-4-(3-methyl-2-pyridyl)-2H-1-benzopyran in the form of an oil.

(E) 2.97 g of 2,2-dimethyl-4-(3-methyl-2-pyridyl)-2H-1-benzopyran were dissolved in 50 ml of ethanol and shaken at room temperature under a hydrogen atmosphere with 10% palladium-on-charcoal in the presence of 0.5 ml of acetic acid. After 24 hours the catalyst was filtered off and the filtrate was evaporated. The residue was chromatographed on silica gel using ethyl acetate/petroleum ether (1:4) for the elution. There were obtained 1.4 g of 3,4-dihydro-2,2-dimethyl-4-(3-methyl-2-pyridyl)-2H-1-benzopyran together with mixed fractions containing this compound and starting material. The procedure described above was carried out on the mixed fractions to give 675 mg of 3,4-dihydro-2,2-dimethyl-4-(3-methyl-2-pyridyl)-2H-1-benzopyran which was recrystallized from t-butyl methyl ether and then melted at 100°-102° C.

(F) 712 mg of 3,4-dihydro-2,2-dimethyl-4-(3-methyl-2-pyridyl)-2H-1-benzopyran were suspended in 10 ml of nitromethane at room temperature. 750 mg of aluminum chloride and then 500 mg of acetyl chloride were added. After 1 hour at room temperature dilute sodium hydroxide solution was added and the mixture was extracted with ethyl acetate. The organic extract was dried over sodium sulphate and evaporated. The residue was chromatographed on silica gel using ethyl acetate/petroleum ether (1:3) and then ethyl acetate/petroleum ether (1:1) for the elution. The resulting oil was triturated with n-hexane to give a solid which, after recrystallization from cyclohexane, yielded 165 mg of 6-acetyl-3,4-dihydro-2,2-dimethyl-4-(3-methyl-2-pyridyl)-2H-1-benzopyran of melting point 87°-88° C.

EXAMPLE 5

248 mg of 3,4-dihydro-2,2-dimethyl-4-(3-methyl-2-pyridyl)-6-nitro-2H-1-benzopyran were dissolved in 20 ml of dichloromethane at room temperature and 222 mg of m-chloroperbenzoic acid were added. After stirring at room temperature overnight the solution was washed in succession with sodium bisulphite solution, sodium bicarbonate solution and water. The organic phase was dried over sodium sulphate and evaporated. The resulting solid was triturated with diethyl ether, filtered off and recrystallized from acetonitrile to give 133 mg of 2-(3,4-dihydro-2,2-dimethyl-6-nitro-2H-1-benzopyran-4-yl)-3-methylpyridine N-oxide of melting point 218°–220° C.

The 3,4-dihydro-2,2-dimethyl-4-(3-methyl-2-pyridyl)-6-nitro-2H-1-benzopyran used as the starting material was prepared as follows:

685 mg of 3,4-dihydro-2,2-dimethyl-4-(3-methyl-2-pyridyl)-2H-1-benzopyran were dissolved in 20 ml of acetonitrile at room temperature and 360 mg of nitronium tetrafluoroborate were added. After 30 minutes the solvent was removed by evaporation and ethyl acetate and water were added. The organic phase was dried over sodium sulphate and evaporated. The residue was chromatographed on silica gel using ethyl acetate/petroleum ether (1:4) for the elution. There were obtained 374 mg of 3,4-dihydro-2,2-dimethyl-4-(3-methyl-2-pyridyl)-6-nitro-2H-1-benzopyran in the form of a solid of melting point 164°–165° C. after recrystallization from t-butyl methyl ether.

EXAMPLE 6

406 mg of m-chloroperbenzoic acid were added to a solution of 524 mg of 2,2-dimethyl-4-(2-pyridyl)-2H-1-benzopyran-6-carbonitrile in 15 ml of dichloromethane at room temperature. After stirring at room temperature for 17 hours the solution was washed with sodium bicarbonate solution. The organic phase was dried over sodium sulphate and evaporated. The residue was chromatographed on silica gel using methanol/ethyl acetate (1:4) for the elution. There were obtained 240 mg of 2-(6-cyano-2,2-dimethyl-2H1-benzopyran-4-yl)pyridine N-oxide of melting point 187°–189° C. after recrystallization from ethyl acetate.

The 2,2-dimethyl-4-(2-pyridyl)-2H-1-benzopyran-6-carbonitrile used as the starting material was prepared according to method (A) or (B) below:

(A) 53 mg of copper(I) iodide, 293 mg of triphenylphosphine and 99 mg of palladium(II) chloride were dissolved in 320 ml of diethylamine. 10.4 g of 4-(1,1-dimethyl-2-propynyloxy)benzonitrile and 11.5 g of 2-iodopyridine were added and the mixture was stirred at room temperature under a nitrogen atmosphere for 3 days. Water and ethyl acetate were added and the organic phase was separated, dried over sodium sulphate and evaporated. The residue was chromatographed on silica gel using ethyl acetate/petroleum ether (1:3) and then ethyl acetate/petroleum ether (1:2) for the elution to give 12.98 g of 4-[1,1-dimethyl 3-(2-pyridyl)-2-propynyloxy] benzonitrile in the form of an oil.

12.98 g of 4-[1,1-dimethyl-3-(2-pyridyl)-2-propynyloxy]benzonitrile were dissolved in 50 ml of 1,2-dichlorobenzene and heated at reflux for 5 hours. After cooling the mixture was evaporated. The residue was chromatographed on silica gel using ethyl acetate/petroleum ether (1:2), ethyl acetate/petroleum ether (1:1) and ethyl acetate for the elution. There were obtained 6.5 g of 2,2-dimethyl-4-(2-pyridyl)-2H-1-benzopyran-6-carbonitrile of melting point 106°–108° C. after recrystallization from cyclohexane.

(B) 280 mg of 2-(6-cyano-3,4-dihydro-2,2-dimethyl-2H-1-benzopyran-4-yl)pyridine N-oxide were heated at 120° C. in 3 ml of acetic anhydride for 24 hours. After cooling the mixture was evaporated and the residue was partitioned between ethyl acetate and aqueous sodium bicarbonate solution. The organic phase was dried over sodium sulphate and evaporated. The residue was recrystallized from cyclohexane to give 181 mg of 2,2-dimethyl-4-(2-pyridyl)-2H-1-benzopyran-6-carbonitrile which was used without further purification.

EXAMPLE 7

406 mg of m-chloroperbenzoic acid were added to a solution of 528 mg of 3,4-dihydro-2,2-dimethyl-4-(2-pyridyl)-2H-1-benzopyran-6-carbonitrile in 15 ml of dichloromethane at room temperature. After 2 hours at room temperature the mixture was washed with sodium bicarbonate solution and the organic phase was dried over sodium sulphate and evaporated. The residue crystallized from t-butyl methyl ether and was recrystallized from toluene to give 360 mg of 2-(6-cyano-3,4-dihydro-2,2-dimethyl-2H-1-benzopyran-4-yl)pyridine N-oxide of melting point 158°–160° C.

The 3,4-dihydro-2,2-dimethyl-4-(2-pyridyl)-2H-1-benzopyran-6-carbonitrile used as the starting material was prepared as follows:

2.96 g of 2,2-dimethyl-4-(2-pyridyl)-2H-1-benzopyran-6-carbonitrile were dissolved in 100 ml of ethanol and added at room temperature to 100 mg of 10% palladium-on-charcoal. The mixture was shaken at room temperature under a hydrogen atmosphere for 2 hours. The catalyst was then removed by filtration and the filtrate was evaporated. The residue was chromatographed on silica gel using ethyl acetate/petroleum ether (1:2) for the elution. There were obtained 2.44 g of 3,4-dihydro-2,2-dimethyl-4-(2-pyridyl)-2H-1-benzopyran-6-carbonitrile of melting point 114°–115° C.

EXAMPLE 8

0.47 g of 2-[1-(2-hydroxy-5-methylthiophenyl)-3-methyl-2-butenyl]pyridine N-oxide was taken up in 10 ml of dichloromethane and stirred with 5 drops of sulphuric acid for 1 hour at 20° C. The mixture was diluted with 20 ml of dichloromethane and washed with aqueous sodium carbonate solution. The organic phase was evaporated and the residue was chromatographed on silica gel using diethyl ether/methanol (19:1) for the elution to give 0.44 g of 2-(3,4-dihydro-2,2-dimethyl-6methylthio-2H-1-benzopyran-4-yl)pyridine N-oxide in the form of a pale yellow oil.

Analysis for $C_{17}H_{19}NO_2S$: Calculated: C:67.7; H:6.35; N:4.65; Found C:67.8; H:6.4; N:4.6%.

The 2-[1-(2-hydroxy-5-methylthiophenyl)-3-methyl-2-butenyl]pyridine N-oxide used as the starting material was prepared as follows (A) 6.54 g of 2-picoline N-oxide were added dropwise to a stirred suspension of 1.8 g of 80% (w/w) sodium hydride in 50 ml of dry tetrahydrofuran. The mixture was stirred at 20° C. for 0.5 hour and then at reflux for 0.5 hour. 15.2 g of ethyl 2-methyl-2-(4-methylthiophenoxy)propionate were then added and the mixture was heated under reflux for a further 18 hours. The solvent was then removed by evaporation and the residue was taken up in water, the pH was adjusted to 5 using 2M hydrochloric acid and the solution was extracted with dichloromethane. The organic phase was evaporated and the residue was chromatographed on silica gel using diethyl ether/methanol (85:15) for the elution to give 10.1 g of 2-[3-methyl-3-[4-(methylthio)-phenoxy]-2-oxobutyl]pyridine N-oxide in the form of a yellow syrup Analysis for $C_{17}H_{19}NO_3S$: Calculated: C:64.3; H:6.0; N:4.4; Found: C:64.1; H:6.0; N:4.3%.

(B) 0.76 g of sodium borohydride was added to a stirred solution of 6.34 g of 2-[3-methyl-3-[4-(methylthio)phenoxy]-2-oxobutyl]pyridine N-oxide in 50 ml of ethanol. The mixture was stirred at 20° C. for 1 hour, 50 ml of water were added and the ethanol was removed by evaporation. The aqueous solution was extracted with ethyl acetate and the organic extract was evaporated to give 5.65 g of 2-[2-hydroxy-3-methyl-3-(4-methylthiophenoxy)butyl]pyridine N-oxide in the form of a white solid of melting point 98°–100° C. (from diethyl ether).

(C) 1.25 g of methanesulphonyl chloride were added dropwise at 20° C. to a stirred solution of 2.73 g of 2-[2-hydroxy-3-methyl-3-(4-methylthiophenoxy) butyl]pyridine N-oxide in 10 ml of pyridine and the mixture was stirred at 20° C. for 16 hours. A further 1.25 g of methanesulphonyl chloride were then added and the stirring was continued for 3 hours. The mixture was then poured into 2M hydrochloric acid and extracted with ethyl acetate. The solvent was removed by evaporation and the residue was crystallized from ethyl acetate to give 0.95 g of 2-[2-methanesulphonyloxy-3-methyl-3-(4-methylthiophenoxy)butyl]pyridine N-oxide methanesulphonic acid salt in the form of a white solid of melting point 126°–128° C.

(D) A solution of 3.35 g of 2-[2-methanesulphonyloxy-3-methyl-3-(4-methylthiophenoxy)butyl]pyridine N-oxide methanesulphonic acid salt and 2.25 g of sodium iodide in 50 ml of acetone was heated under reflux for 2 hours. The mixture was filtered and the filtrate was evaporated. The residue was partitioned between water and dichloromethane and the organic phase was evaporated. The residue was taken up in 50 ml of acetone and heated under reflux for 2 hours with 2.25 g of sodium iodide. The cooled reaction mixture was then evaporated and the residue was partitioned between water and dichloromethane. The organic phase was evaporated and the residue was crystallized from dichloromethane/ethyl acetate to give 1.8 g of 2-[2-iodo-3-methyl-3-(4-methylthiophenoxy)butyl]pyridine N-oxide in the form of a pale yellow solid of melting point 191°–193° C.

(E) A solution of 0.86 g of 2-[2-iodo-3 -methyl-3-(4methylthiophenoxy)butyl]pyridine N-oxide and 2 ml of diisopropylethylamine in 10 ml of ethanol was heated under reflux for 24 hours. The solvent was then removed by evaporation and the residue was partitioned between 2M hydrochloric acid and dichloromethane. The organic phase was evaporated and the residue was recrystallized from ethyl acetate/n-hexane to give 0.47 g of 2-[1-(2-hydroxy-5-methylthiophenyl)-3-methyl-2-butenyl]pyridine N-oxide in the form of an off-white solid.

EXAMPLE 9

A solution of 0.45 g of 2-(3,4-dihydro-2,2-dimethyl-6-methylthio-2H-1-benzopyran-4-yl)pyridine N-oxide and 0.645 g of m-chloroperbenzoic acid in 10 ml of dichloromethane was stirred at 20° C. for 16 hours. The mixture was then diluted with 20 ml of dichloromethane, the resulting solution was washed with aqueous sodium carbonate solution and sodium chloride solution and then evaporated. The residue was crystallized from ethyl acetate to give 0.446 g of 2-(3,4-dihydro-2,2-dimethyl-6-methylsulphonyl-2H-1-benzopyran-4-yl)pyridine N-oxide in the form of a white solid of melting point 213°–214° C.

EXAMPLE 10

1.61 g of 2.2-dimethyl-4-(2-pyridyl)-2H-1-benzopyran were dissolved in 10 ml of dichloromethane at room temperature and 2.0 g of m-chloroperbenzoic acid were added. After 1 hour the mixture was washed with sodium bisulphite solution, sodium bicarbonate solution and water. The organic phase was dried over sodium sulphate and evaporated. The residue was chromatographed on silica gel using ethyl acetate/ethanol/formic acid (40:4:1) for the elution. The product was obtained as an oil which solidified upon trituration with diethyl ether. Recrystallization from toluene gave 0.034 g of 2-(2,2-dimethyl-2H-1-benzopyran-4-yl)pyridine N-oxide of melting point 148°–150° C.

EXAMPLE 11

330 mg of 6-bromo-3,4-dihydro-2,2-dimethyl-4-(2-pyridyl)-2H-1-benzopyran were dissolved in 10 ml of dichloromethane at room temperature and 280 mg of m-chloroperbenzoic acid were added. After stirring at room temperature for 3 days the mixture was washed with sodium bisulphite solution, then with sodium bicarbonate solution and finally with water. The organic phase was dried over sodium sulphate and evaporated. The residue was chromatographed on silica gel using 4% (v/v) methanol/ethyl acetate for the elution to give 250 mg of 2-(6-bromo-3,4-dihydro-2,2-dimethyl-2H-1-benzopyran-4-yl)pyridine N-oxide as a foam. NMR (300 MHz, CDCl$_3$): 8.35–8.30 (1H, m), 7.26–7.15 (3H, m), 7.13–7.05 (1H, m), 6.95 (1H, broad s), 6.75 (1H, d, 9Hz), 5.28 (1H, broad s), 2.42 (1H, dd, 13Hz, 6Hz), 1.7 (1H, broad s), 1.42 (3H, s), 1.37 (3H, s). MS (EI): 335 (M+[Br$^{81}$], 333 (H+[Br$^{79}$]), 318 (M+[Br$^{81}$]-OH), 316 (M+[Br$^{79}$]-OH)

The 6-bromo-3,4-dihydro-2,2-dimethyl-4-(2-pyridyl)-2H-1-benzopyran used as the starting material was prepared as follows:

0.5 g of 3,4-dihydro-2,2-dimethyl-4-(2-pyridyl)-2H-1-benzopyran was dissolved in 10 ml of carbon tetrachloride at room temperature and 0.25 ml of pyridine and 0.12 ml of bromine were added. The mixture was stirred at room temperature for 1 hour, then at 35° C. for 1 hour and finally at 65° C. for 1 hour. After cooling the mixture was washed with sodium bicarbonate solution, the aqueous washings were extracted with dichloromethane and the combined organic phases were washed with water, dried over sodium sulphate and evaporated. The residue was chromatographed on silica gel using 2% (v/v) methanol/dichloromethane for the elution. The product was recrystallized from t-butyl methyl ether to give 230 mg of 6-bromo-3,4-dihydro-2,2-dimethyl)-4-(2-pyridyl)-2H-1-benzopyran of melting point 134°–136° C.

EXAMPLE 12

402 mg of methyl 2,2-dimethyl-4-(2-pyridyl)-2H-1-benzopyran-6-carboxylate were dissolved in 15 ml of dichloromethane at room temperature and 330 mg of m-chloroperbenzoic acid were added. After stirring at room temperature overnight the mixture was washed with sodium bisulphite solution and sodium bicarbonate solution, dried over sodium sulphate and evaporated. The residue was chromatographed on silica gel using 10% (v/v) methanol/ethyl acetate for the elution. The product was recrystallized from t-butyl methyl ether to give 65 mg of 2-[6-(methoxycarbonyl)-2,2-dimethyl-2H-

1-benzopyran-4-yl]pyridine N-oxide of melting point 155°–157° C.

The methyl 2,2-dimethyl-4-(2-pyridyl)-2H-1-benzopyran-6-carboxylate used as the starting material was prepared as follows:

(A) 2.2 g of 2,2-dimethyl-4-(2-pyridyl)-2H-1-benzopyran-6-carbonitrile were suspended in 40 ml of 0.5M sodium hydroxide solution and heated to reflux for 18 hours. The mixture was allowed to cool to room temperature and was then extracted with ethyl acetate. The aqueous phase was acidified to pH 6 with citric acid, whereupon a solid crystallized out. This solid was filtered off, washed with diethyl ether and recrystallized from ethanol to give 1.27 g of 2,2-dimethyl-4-(2-pyridyl)-2H-1-benzopyran-6-carboxylic acid of melting point 238°–240° C.

(B) 0.65 g of 2,2-dimethyl-4-(2-pyridyl)-2H-1-benzopyran-6-carboxylic acid was dissolved in 10 ml of thionyl chloride and stirred at room temperature for 1 hour. The mixture was evaporated, 5 ml of methanol were added and the mixture was again evaporated. The residue was partitioned between diethyl ether and aqueous sodium hydroxide solution. The organic phase was separated, dried over sodium sulphate and evaporated. The residue was chromatographed on silica gel using ethyl acetate/petroleum ether (1:1) for the elution. The product was recrystallized from cyclohexane to give 345 mg of methyl 2,2-dimethyl-4-(2-pyridyl)-2H-1-benzopyran-6-carboxylate of melting point 94°–95° C.

EXAMPLE 13

313 mg of methyl 3,4-dihydro-2,2-dimethyl-4-(2-pyridyl)-2H-1-benzopyran-6-carboxylate were dissolved in 10 ml of dichloromethane at room temperature and 283 mg of m-chloroperbenzoic acid were added. After stirring at room temperature for 2 hours the mixture was washed with sodium bisulphite solution and sodium bicarbonate solution. The organic phase was dried over sodium sulphate and evaporated. The residue was chromatographed on silica gel using initially 2% (v/v) methanol/ethyl acetate and finally 5% (v/v) methanol/ethyl acetate for the elution. There were obtained 250 mg of 2-[3,4-dihydro-6-(methoxycarbonyl)-2,2-dimethyl-2H-1-benzopyran-4-yl]pyridine N-oxide as an oil which solidified upon trituration with diethyl ether. After recrystallization from toluene the product melted at 128°–130° C.

The methyl 3,4-dihydro-2,2-dimethyl-4-(2-pyridyl)-2H-1-benzopyran-6-carboxylate used as the starting material was prepared as follows:

(A) 2.44 g of 3,4-dihydro-2,2-dimethyl-4-(2-pyridyl)-2H-1-benzopyran-6-carbonitrile were suspended in 100 ml of 0.37M sodium hydroxide solution and heated at reflux overnight. The resulting solution was extracted with ethyl acetate and the aqueous phase was acidified with citric acid. The precipitated solid was filtered off and washed with water and with diethyl ether There were obtained 1.6 g of 3,4-dihydro-2,2-dimethyl-4-(2-pyridyl)-2H-1-benzopyran-6-carboxylic acid of melting point 207°–208° C.

(B) 0.8 g of 3,4-dihydro-2,2-dimethyl-4-(2-pyridyl)-2H-1-benzopyran-6-carboxylic was stirred at room temperature in 10 ml of thionyl chloride. The reaction was followed by thin-layer chromatography on silica gel using ethyl acetate/ethanol/formic acid (40:4:1) for the elution. After completion of the reaction the mixture was evaporated, toluene was added, the mixture was evaporated, methanol was added and the mixture was again evaporated. The residue was partitioned between diethyl ether and sodium bicarbonate solution. The organic phase was dried over sodium sulphate and evaporated. The residue was chromatographed on silica gel using ethyl acetate/petroleum ether (1:1) for the elution to give 430 mg of methyl 3,4-dihydro-2,2-dimethyl-4-(2-pyridyl)-2H-1-benzopyran-6-carboxylate which, after recrystallization from cyclohexane, melted at 113°–115° C.

EXAMPLE 14

564 mg of 3,4-dihydro-2,2-dimethyl-4-(2-pyridyl)-2H-1-benzopyran-6-carboxamide were dissolved in 20 ml of dichloromethane at room temperature and 540 mg of m-chloroperbenzoic acid were added. After stirring at room temperature overnight the mixture was washed with sodium bisulphite solution, sodium bicarbonate solution and water. The organic phase was dried over sodium sulphate and evaporated to give a solid which was recrystallized from isopropanol to yield 164 mg of 2-(6-carbamoyl-3,4-dihydro-2,2-dimethyl-2H-1-benzopyran-4-yl)pyridine N-oxide of melting point 248°–250° C.

The 3,4-dihydro-2,2-dimethyl-4-(2-pyridyl)-2H-1-benzopyran-6-carboxamide used as the starting material was prepared as follows:

803 mg of 3,4-dihydro-2,2-dimethyl-4-(2-pyridyl)-2H-1-benzopyran-6-carboxylic acid were dissolved in 10 ml of thionyl chloride and stirred at room temperature for 1 hour. The mixture was evaporated, the residue was dissolved in toluene and the solution was again evaporated. The residue was treated with 0.88 ammonia and the mixture was partitioned between ethyl acetate and sodium bicarbonate solution. The organic phase was washed with water and sodium chloride solution, dried over sodium sulphate and evaporated. The residue was recrystallized from ethanol to give 400 mg of 3,4-dihydro-2,2-dimethyl-4-(2-pyridyl)-2H-1-benzopyran-6-carboxamide of melting point 225°–227° C.

EXAMPLE 15

In an analogous manner to that described in the first paragraph of Example 11, from 6-chloro-3,4-dihydro-2,2-dimethyl-4-(2-pyridyl)-2H -1-benzopyran there was obtained 2-(6-chloro-3,4-dihydro-2,2-dimethyl-2H-1-benzopyran4-yl)pyridine N-oxide in the form of a foam. NMR(300 MHz, CDCl$_3$): $\delta$8.36–8.30 (1H, m), 7.26–7.18 (2H, m), 7.14–7.05 (2H, m), 6.84–6.75 (2H, m), 5.29 (1H, broad s), 2.42 (1H, dd, 12.5Hz, 6Hz), 1.76 (1H, broad s), 1.44 (3H, s), 1.39 (3H, s). MS (EI): 289 (M ]), 272 (M+[Cl$_{35}$]-OH).

The 6-chloro-3,4-dihydro-2,2-dimethyl-4-(2-pyridyl)-2H-1-benzopyran used as the starting material was prepared as follows:

1 g of 3,4-dihydro-2,2-dimethyl-4-(2-pyridyl)-2H-1-benzopyran was dissolved in 20 ml of carbon tetrachloride at room temperature and 0.25 ml of pyridine and 10 ml of a 0.42M solution of chlorine in carbon tetrachloride were added. After 30 minutes the mixture was washed with sodium bicarbonate solution, the organic phase was separated, dried over sodium sulphate and evaporated. The residue was chromatographed on silica gel using 1% (v/v) methanol/dichloromethane and then 2% (v/v) methanol/dichloromethane for the elution. The product was recrystallized from t-butyl methyl ether to give 200 mg of 6-chloro-3,4-dihydro-2,2-dimethyl-4-(2-pyridyl)-2H-1-benzopyran of melting point 124°–125° C.

EXAMPLE 16

In an analogous manner to that described in the first paragraph of Example 11, from 4-(2-pyridyl)-2,2,6-trimethyl-2H-1-benzopyran there was obtained 2-(2,2,6-trimethyl-2H-1-benzopyran-4-yl)pyridine N-oxide of melting point 189°-191° C. after recrystallization from ethyl acetate.

The 4-(2-pyridyl)-2,2,6-trimethyl-2H-1-benzopyran used as the starting material was prepared from 2-bromo-4methylanisole and 2-cyanopyridine in an analogous manner to that described in Example 4 (A)-(D).

EXAMPLE 17

In an analogous manner to that described in the first paragraph of Example 6, from 2,2-dimethyl-4-(2-pyridyl)-6-(trifluoromethyl)-2H-1-benzopyran there was obtained 2-[6-(trifluoromethyl)-2,2-dimethyl-2H-1-benzopyran-4-yl]pyridine N-oxide of melting point 149°-152° C. after recrystallization from cyclohexane.

The 2,2-dimethyl-4-(2-pyridyl)-6-trifluoromethyl-2H-1-benzopyran used as the starting material was prepared as follows:

(A) 1.62 g of 4-(trifluoromethyl)phenol, 1.53 g of 2-chloro-2-methyl-3-butyne and 10 g of potassium carbonate were heated at reflux in 50 ml of acetone. After 18, 42 and 66 hours further batches of 1 53 g of 2-chloro-2-methyl-3-butyne were added. 72 hours after the final addition the mixture was allowed to cool to room temperature and was partitioned between diethyl ether and water. The organic phase was washed with aqueous sodium hydroxide solution, dried over sodium sulphate and evaporated. The residue was chromatographed on silica gel using 5% (v/v) ethyl acetate/petroleum ether for the elution. 1.8 g of 4-(1,1-dimethyl-2-propynyloxy)-trifluoromethylbenzene were obtained as a yellow oil.

(B) The 4-(1,1-dimethyl-2-propynyloxy)trifluoromethylbenzene was converted into 2,2-dimethyl-4-(2-pyridyl)-6-trifluoromethyl-2H-1-benzopyran in an analogous manner to that described in Example 6(A).

EXAMPLE 18

In an analogous manner to that described in the first paragraph of Example 3, from 6-(t-butyl)-3,4-dihydro-2,2-dimethyl-4-(2-pyridyl)-2H-1-benzopyran there was obtained 2-[6-(t-butyl)-3,4-dihydro-2,2-dimethyl-2H-1-benzopyran 4-yl]pyridine N-oxide in the form of a white solid of melting point 128°-130° C. after recrystallization from cyclohexane.

The 6-(t-butyl)-3,4-dihydro-2,2-dimethyl-4-(2-pyridyl)-2H-1-benzopyran used as the starting material was prepared in an analogous manner to that described in the last paragraph of Example 3, but using pivaloyl chloride in place of acetyl chloride.

EXAMPLE 19

94 mg of 6-benzoyl-3,4-dihydro-2,2-dimethyl-4-(2-pyridyl)-2H-1-benzopyran and 52 mg of m-chloroperbenzoic acid were stirred in 15 ml of dichloromethane at room temperature until thin-layer chromatography indicated that the reaction was complete. The mixture was washed in succession with sodium bisulphite solution and sodium bicarbonate solution, then dried over sodium sulphate and evaporated. The residue was chromatographed on silica gel using 10% (v/v) methanol/ethyl acetate for the elution. After trituration with diethyl ether there were obtained 20 mg of 2-(6-benzoyl-3,4-dihydro-2,2-dimethyl-2H-1-benzopyran-4-yl)pyridine N-oxide of melting point 134°-136° C.

The 6-benzoyl-3,4-dihydro-2.2-dimethyl-4-(2-pyridyl)-2H-1-benzopyran used as the starting material was prepared as follows:

264 mg of aluminum chloride were added to an ice-cooled solution of 237 mg of 3,4-dihydro-2,2-dimethyl-4-(2-pyridyl)-2H-1-benzopyran in 6 ml of nitromethane. The mixture was stirred for 5 minutes, 349 mg of benzoyl chloride were added and the stirring was continued at 0° C. for 30 minutes and at room temperature for 16 hours. The o reaction mixture was diluted with diethyl ether and washed with sodium hydroxide solution. The organic phase was dried over sodium sulphate and evaporated. The residue was chromatographed on silica gel using ethyl acetate/petroleum ether (2:3) for the elution to give 94 mg of 6-benzoyl-3,4-dihydro-2,2-dimethyl-4-(2-pyridyl)-2H-1-benzopyran.

EXAMPLE 20

134 mg of 3,4-dihydro-2,2-dimethyl-6-(4-nitrobenzoyl)-4-(2-pyridyl)-2H-1-benzopyran were dissolved in 15 ml of dichloromethane and 72 mg of m-chloroperbenzoic acid were added. The mixture was stirred at room temperature overnight. After washing in succession with sodium bisulphite solution and sodium bicarbonate solution the organic phase was dried over sodium sulphate and evaporated. The residue was chromatographed on silica gel using ethyl acetate/methanol (4:1) for the elution. The residue was recrystallized from isopropanol to give 50 mg of 2-[3,4-dihydro-2,2-dimethyl-6-(4-nitrobenzoyl)-2H-1-benzopyran-4-yl]pyridine N-oxide of melting point 209°-211° C.

The 3,4-dihydro-2,2-dimethyl-6-(4-nitrobenzoyl)-4-(2-pyridyl)-2H-1-benzopyran used as the starting material was prepared as follows:

200 mg of 3,4-dihydro-2,2-dimethyl-4-(2-pyridyl)-2H-1-benzopyran were dissolved in 10 ml of nitromethane and the solution was cooled to 0° C. under a nitrogen atmosphere. 240 mg of finely powdered aluminum chloride were added and, after stirring at 0° C. for 5 minutes, 388 mg of 4-nitrobenzoyl chloride were added. After 16 hours at room temperature 120 mg of aluminum chloride were added and the mixture was stirred at 100° C. for 45 minutes. After dilution with diethyl ether and washing with sodium hydroxide solution the organic phase was dried over sodium sulphate and evaporated. The residue crystallized and was triturated with diethyl ether to give 150 mg of 3,4-dihydro-2,2-dimethyl-6-(4-nitrobenzoyl)-4-(2 -pyridyl)-2H-1benzopyran.

EXAMPLE 21

207 mg of 3,4-dihydro-2,2-dimethyl-6-(2-iodobenzoyl)-4-(2-pyridyl)-2H-1-benzopyran were stirred in 15 ml of dichloromethane with 76 mg of m-chloroperbenzoic acid for 3 hours. The mixture was washed in succession with sodium bisulphite solution and sodium bicarbonate solution, the organic phase was dried over sodium sulphate and evaporated. The residue was chromatographed on silica gel using 13% (v/v) methanol/ethyl acetate for the elution to give, after recrystallization from diethyl ether, 15 mg of 2-[3,4-dihydro-2,2-dimethyl-6-(2-iodobenzoyl)-2H-1-benzopyran-4-yl]pyridine N-oxide of melting point 114°-120° C.

The 3,4-dihydro-2,2-dimethyl-6-(2-iodobenzoyl)-4-(2-pyridyl)-2H-1-benzopyran used as the starting material was prepared as follows:

250 mg of 3,4-dihydro-2,2-dimethyl-4-(2-pyridyl)-2H-1benzopyran were dissolved in 10 ml of nitromethane and cooled in an ice-bath under a nitrogen atmosphere. 280 mg of finely powdered aluminum chloride were added followed, after 5 minutes, by 700 mg of 2-iodobenzoyl chloride. After stirring at 0° C. for 30 minutes and at room temperature for 1 hour the mixture was diluted with diethyl ether and washed with sodium hydroxide solution. The organic phase was dried over sodium sulphate and evaporated. The residue was chromatographed on silica gel using ethyl acetate/petroleum ether (1:2) for the elution to give 230 mg of 3,4-dihydro-2,2-dimethyl-6-(2-iodobenzoyl)-4-(2-pyridyl)-2H-1-benzopyran.

EXAMPLE 22

In an analogous manner to that described in the first paragraph of Example 21, from 3,4-dihydro-2,2-dimethyl-6-(3-iodobenzoyl)-4-(2-pyridyl)-2H-1-benzopyran there was obtained 2-[3,4-dihydro-2,2-dimethyl-6-(3-iodobenzoyl)-2H-1-benzopyran-4-yl]pyridine N-oxide of melting point 128°-130° C. (from cyclohexane/ethyl acetate).

The 3,4-dihydro-2,2-dimethyl-6-(3-iodobenzoyl)-4-(2-pyridyl)-2H-1-benzopyran used as the starting material was prepared in an analogous manner to that described in the last paragraph of Example 21 using 3-iodobenzoyl chloride in place of 2-iodobenzoyl chloride.

EXAMPLE 23

In an analogous manner to that described in the first paragraph of Example 21, from 3,4-dihydro-2,2-dimethyl-6-(4-iodobenzoyl)-4-(2-pyridyl)-2H-1-benzopyran there was obtained 2-[3,4-dihydro-2,2-dimethyl-6-(4-iodobenzoyl)-2H-1-benzopyran-4-yl]pyridine N-oxide of melting point 171°-173° C. (from ethyl acetate).

The 3,4-dihydro-2,2-dimethyl-6-(4-iodobenzoyl)-4-(2-pyridyl)-2H-1-benzopyran used as the starting material was prepared in an analogous manner to that described in the last paragraph of Example 21 using 4-iodobenzoyl chloride in place of 2-iodobenzoyl chloride.

EXAMPLE 24

In an analogous manner to that described in the first paragraph of Example 6, from 2-ethyl-2-methyl-4-(2-pyridyl)-2H-1-benzopyran-6-carbonitrile there was obtained 2-(6-cyano-2-ethyl-2-methyl-2H-1-benzopyran-4-yl)pyridine N-oxide of melting point 129°-131° C. (from ethyl acetate/petroleum ether).

The 2-ethyl-2-methyl-4-(2-pyridyl)-2H-1-benzopyran-6-carbonitrile used as the starting material was prepared as follows:

(A) 17.47 g of 2-chloro-2-methylpent-1-yne were added to a mixture of 11.9 g of 4-cyanophenol, 6.0 g of sodium hydroxide, 15 ml of a 40% methanolic solution of benzyltrimethylammonium hydroxide in 85 ml of water and 85 ml of dichloromethane and stirred for 4 days. The organic phase was separated, washed with 2M sodium hydroxide solution, dried over sodium sulphate and evaporated. The residue was chromatographed on silica gel using ethyl acetate/petroleum ether (1:9) for the elution to give 10.1 g of 4-(1-ethyl-1-methyl-2-propynyloxy)benzonitrile.

(B) 4-(1-Ethyl-1-methyl-2-propynyloxy)benzonitrile was converted into 2-ethyl-2-methyl-4-(2-pyridyl)-2H-benzopyran-6-carbonitrile in an analogous manner to that described in Example 6(A).

EXAMPLE 25

In an analogous manner to that described in the first paragraph of Example 4, from 6-acetyl-2-methyl-4-(2-pyridyl)-2H-1-benzopyran there was obtained 2-(6-acetyl-2-methyl-2H-1-benzopyran-4-yl)pyridine N-oxide of melting point 170°-172° C. (from toluene).

The 6-acetyl-2-methyl-4-(2-pyridyl)-2H-1-benzopyran used as the starting material was prepared from 1-bromo-2-methylprop-1-ene and 2-methoxyphenyl 2-pyridyl ketone in an analogous manner to that described in Example 1 (A)-(D).

EXAMPLE 26

152 mg of 4-(6-chloro-2-pyridyl)-3,4-dihydro-2,2-dimethyl-2H-1-benzopyran-6-carbonitrile and 136 mg of m-chloroperbenzoic acid were heated at reflux in 15 ml of chloroform. After 10 hours and 20 hours 80 mg and 50 mg, respectively., of m-chloroperbenzoic acid were added. After 30 hours the mixture was allowed to cool to room temperature, washed in succession with sodium bisulphite solution and sodium bicarbonate solution, dried over sodium sulphate and evaporated. The residue was chromatographed on silica gel using ethyl acetate for the elution to give, after trituration with n-hexane, a solid which was recrystallized from acetonitrile. There were obtained 33 mg of 2-chloro-6-(6-cyano-3,4-dihydro-2,2-dimethyl-2H-1-benzopyran-4-yl)pyridine N-oxide of melting point 195°-196° C.

The 4-(6-chloro-2-pyridyl)-3,4-dihydro-2,2-dimethyl-2H-1-benzopyran-6-carbonitrile used as the starting material was prepared as follows:

1 g of 2-(6-cyano-3,4-dihydro-2,2-dimethyl-2H-1-benzopyran-4-yl)pyridine N-oxide was dissolved in 15 ml of phosphorus oxychloride, heated at 80° C. for 2 hours and allowed to cool to room temperature overnight. The phosphorus oxychloride was removed in vacuo and the residue was taken up in sodium bicarbonate solution and ethyl acetate. The aqueous phase was extracted several times with ethyl acetate and the combined ethyl acetate solutions were dried over sodium sulphate and evaporated. The residue was chromatographed on silica gel. Elution with ethyl acetate/petroleum ether (1:4) gave 271 mg of 4-(6-chloro-2-pyridyl)-3,4-dihydro-2,2-dimethyl-2H-1-benzopyran-6-carbonitrile and elution with ethyl acetate/petroleum ether (1:2) gave 170 mg of 4-(4-chloro-2-pyridyl)-3,4-dihydro-2,2-dimethyl-2H-1 -benzopyran-6carbonitrile.

EXAMPLE 27

79 mg of 4-(4-chloro-2-pyridyl)-3,4-dihydro-2,2-dimethyl-2H-1-benzopyran-6-carbonitrile were dissolved in 10 ml of dichloromethane and 70 mg of m-chloroperbenzoic acid were added. The mixture was stirred at room temperature for 3 days, then washed in succession with sodium bisulphite solution, sodium bicarbonate solution and water, dried over sodium sulphate and evaporated. The residue was chromatographed on silica gel using 1% (v/v) methanol/ethyl acetate for the elution to give, after trituration with diethyl ether, a solid which was recrystallized from ethyl acetate/petroleum ether. There being obtained 20 mg of 4-chloro-2-(6-cyano-3,4-dihydro-2,2-dimethyl-2H-1-benzopyran-4-yl)pyridine N-oxide of melting point 173°-174° C.

EXAMPLE 28

250 mg of 4-chloro-2-(6-cyano-3,4-dihydro-2,2-dimethyl-2H-1-benzopyran-4-yl)pyridine N-oxide were dissolved in 6 ml of methanol and added to a solution of sodium methoxide prepared from 0.5 g of metallic sodium in 50 ml of methanol. The mixture was heated at reflux for 2 hours under a nitrogen atmosphere and then allowed to cool to room temperature. The solution was evaporated and the residue was taken up in ethyl acetate and water, the organic phase was separated, dried over sodium sulphate and evaporated. The residue was chromatographed on silica gel using 20% (v/v) methanol/ethyl acetate for the elution to give a solid which was recrystallized from ethyl acetate. There were obtained 65 mg of 2-(6-cyano-3,4-dihydro-2,2-dimethyl-2H-1-benzopyran-4 -yl)-4-methoxypyridine N-oxide of melting point 196°–198° C.

EXAMPLE 29

406 mg of m-chloroperbenzoic acid were added to a solution of 554 mg of 4-(6-amino-2-pyridyl)-2,2-dimethyl-2H-1-benzopyran-6-carbonitrile in 10 ml of dichloromethane and the mixture was stirred for 3 hours. The mixture was then washed with sodium bicarbonate solution, dried over sodium sulphate and evaporated. The residue was chromatographed on silica gel using methanol/ethyl acetate (1:4) for the elution to give a solid which was triturated with dichloromethane and recrystallized from isopropanol. There were obtained 130 mg of 2-amino-6-(6-cyano-2,2-dimethyl-2H-1-benzopyran-4-yl)pyridine N-oxide of melting point 241°–242° C.

The 4-(6-amino-2-pyridyl)-2,2-dimethyl-2H-1-benzopyran-6-carbonitrile used as the starting material was prepared from 4-(1,1-dimethyl-2-propynyloxy)benzonitrile and 2-amino-6-iodopyridine in an analogous manner to that described in Example 6(A).

EXAMPLE 30

In an analogous manner to that described in the first paragraph of Example 7, from 4-(6-amino-2-pyridyl)-3,4-dihydro-2,2-dimethyl-2H-1-benzopyran -6-carbonitrile there was obtained 2-amino-6-(6-cyano-3,4-dihydro-2,2-dimethyl-2H-1-benzopyran-4-yl)pyridine N-oxide of melting point 210°–212° C. (from isopropanol).

The 4-(6-amino-2-pyridyl)-3,4-dihydro-2,2-dimethyl-2H-1-benzopyran-6-carbonitrile used as the starting material was prepared from 4-(6-amino-2-pyridyl)-2,2-dimethyl-2H-1-benzopyran-6-carbonitrile in an analogous manner to that described in the last paragraph of Example 7.

EXAMPLE 31

350 mg of 2-[1-(5-cyano-2-hydroxyphenyl)-3-methyl-2butenyl]-6-methylpyridine N-oxide in 15 ml of dichloromethane were stirred with 100 μl of concentrated sulphuric acid for 1 hour. A further 100 μl of concentrated sulphuric acid were added and stirring was continued for 30 minutes. The mixture was washed with water, dried over sodium sulphate and evaporated. The residue was chromatographed on silica gel using methanol/ethyl acetate (1:9) for the elution to give an oil which crystallized from diethyl ether. There was obtained 0.26 g of 2-(6-cyano-3,4-dihydro-2,2-dimethyl-2H-1-benzopyran-4-yl)-6-methylpyridine N-oxide of melting point 165-167° C.

The 2-[1-(5-cyano-2-hydroxyphenyl)-3-methyl-2butenyl]-6-methylpyridine N-oxide used as the starting material was prepared as follows:

(A) 3.69 g of 2,6-lutidine N-oxide in 15 ml of dry tetrahydrofuran were added at −78° C. under a nitrogen atmosphere to a stirred solution of lithium diisopropylamide (prepared from 3.03 g of diisopropylamine and 18.75 ml of a 1.6M solution of n-butyllithium in n-hexane) in 75 ml of tetrahydrofuran. The mixture was stirred for 30 minutes and then 6.99 g of ethyl 2-methyl-2-(4-cyanophenoxy)propionate in 15 ml of tetrahydrofuran were added. The mixture was allowed to warm to room temperature and was then stirred for 1 hour before being taken up in ethyl acetate and water. The organic phase was separated, dried over sodium sulphate and evaporated. The residue was chromatographed on silica gel using methanol/ethyl acetate (1:4) for the elution to give, after recrystallization from isopropanol, 7.9 g of 2-[3-(4-cyanophenoxy)-3-methyl-2-oxobutyl]-6-methylpyridine N-oxide of melting point 127°–129° C.

(B) 7.3 q of 2-[3-(4-cyanophenoxy)-3-methyl-2-oxobutyl]-6-methylpyridine N-oxide in 160 ml of ethanol were treated with 0.96 g of sodium borohydride and the mixture was stirred for 30 minutes. The solvent was removed by evaporation and the residue was taken up in water and dichloromethane. The organic phase was separated, dried over sodium sulphate and evaporated. The residue was crystallized from diethyl ether to give 7.1 g of 2-[3-(4-cyanophenoxy)-2-hydroxy-3-methylbutyl]-6-methylpyridine N-oxide of melting point 89°–92° C.

(C) 573 mg of methanesulphonyl chloride were added to a stirred solution of 1.56 g of 2-[3-(4-cyanophenoxy)-2-hydroxy-3-methylbutyl]-6-methylpyridine N-oxide in 3 ml of triethylamine and 25 ml of dichloromethane at room temperature. After 1 hour a further 573 mg of methanesulphonyl chloride were added and the mixture was stirred until thin-layer chromatography indicated that the reaction was complete. The mixture was washed with dilute hydrochloric acid and 2M sodium hydroxide solution, dried over sodium sulphate and evaporated to give 1.8 g of 2-[3-(4-cyanophenoxy)-2-methanesulphonyloxy-3-methylbutyl]-6methylpyridine N-oxide.

(D) 1.7 g of 2-[3-(4-cyanophenoxy)-2-methanesulphonyloxy-3-methylbutyl]-6-methylpyridine N-oxide were added to a solution of 200 mg of 80% sodium hydride in 25 ml of isopropanol and the mixture was stirred for 30 minutes. The solvent was removed by evaporation and the residue was partitioned between water and dichloromethane. The organic phase was dried over sodium sulphate and evaporated. The residue was chromatographed on silica gel using 10% (v/v) methanol/ethyl acetate for the elution. There were obtained 960 mg of 2-[3-(4-cyanophenoxy)-3-methyl-1butenyl]-6-methylpyridine N-oxide as a colourless gum.

(E) 850 mg of 2-[3-(4-cyanophenoxy)-3-methyl-1-butenyl]-6-methylpyridine N-oxide in 10 ml of 1,2-dichlorobenzene were heated at 150° C. for 1 hour. The solvent was removed by evaporation to give a solid which was triturated with diethyl ether and then filtered off. There were obtained 600 mg of 2-[1-(5-cyano-2-hydroxyphenyl)-3-methyl-2butenyl]-6-methylpyridine N-oxide which was used without further purification. A sample recrystallized from isopropanol melted at 214°–215° C.

EXAMPLE 32

406 mg of m-chloroperbenzoic acid were added to a solution of 552 mg of 2,2-dimethyl-4-(4-methyl-2-pyridyl)-2H-1-benzopyran-6-carbonitrile in 20 ml of dichloromethane and the mixture was stirred for 1 hour. Subsequently, the mixture was washed with sodium bicarbonate solution, dried over sodium sulphate and evaporated. The residue was chromatographed on silica gel using methanol/ethyl acetate (1:4) for the elution. After recrystallization from ethyl acetate there were obtained 140 mg of 2-(6-cyano-2,2-dimethyl-2H-1-benzopyran-4-yl)-4-methylpyridine N-oxide of melting point 199°–201° C.

The 2,2-dimethyl-4-(4-methyl-2-pyridyl)-2H-1-benzopyran-6-carbonitrile used as the starting material was prepared from 2-iodo-4-methylpyridine and 4-(1,1-dimethyl-2-propynyloxy)benzonitrile in an analogous manner to that described in Example 6(A).

EXAMPLE 33

In an analogous manner to that described in the first paragraph of Example 7, from 3,4-dihydro-2,2-dimethyl-4-(4-methyl-2-pyridyl)-2H-1-benzopyran-6-carbonitrile there was obtained 2-(6-cyano-3,4-dihydro-2,2-dimethyl-2H-1-benzopyran-4-yl)-4-methylpyridine N-oxide of melting point 156°–159° C. (from diethyl ether).

The 3,4-dihydro-2,2-dimethyl-4-(4-methyl-2-pyridyl)-2H-1-benzopyran-6-carbonitrile used as the starting material was prepared from 2,2-dimethyl-4-(4-methyl-2-pyridyl)-2H-1-benzopyran-6-carbonitrile in an analogous manner to that described in the last paragraph of Example 7.

EXAMPLE 34

1 g of 2,2-dimethyl-4-(5-methyl-2-pyridyl)-2H-1-benzopyran-6-carbonitrile and 0.62 g of m-chloroperbenzoic acid were dissolved in 30 ml of dichloromethane and the mixture o was stirred at room temperature for 3 hours. The mixture was washed with sodium bicarbonate solution, dried over sodium sulphate and evaporated. The residue was chromatographed on silica gel using 20% (v/v) methanol/ethyl acetate for the elution to give, after recrystallization from ethyl acetate, 280 mg of 2-(6-cyano-2,2-dimethyl-2H-1-benzopyran-4-yl)-5-methylpyridine N-oxide of melting point 151°–154° C.

The 2,2-dimethyl-4-(5-methyl-2-pyridyl)-2H-1-benzopyran-6-carbonitrile used as the starting material was prepared from 2-iodo-5-methylpyridine and 4-(1,1-dimethyl-2-propynyloxy)benzonitrile in an analogous manner to that described in Example 6(A).

EXAMPLE 35

In an analogous manner to that described in the first paragraph of Example 7, from 3,4-dihydro-2,2-dimethyl-4-(5-methyl-2-pyridyl)-2H-1-benzopyran-6-carbonitrile there was obtained 2-(6-cyano-3,4-dihydro-2,2-dimethyl-2H-1-benzopyran-4-yl)-5-methylpyridine N-oxide of melting point 151°–153° C. (from ethyl acetate and cyclohexane).

The 3,4-dihydro-2,2-dimethyl-4-(5-methyl-2-pyridyl)-2H-1-benzopyran-6-carbonitrile used as the starting material was prepared from 2,2-dimethyl-4-(5-methyl-2-pyridyl)-2H-1-benzopyran-6-carbonitrile in an analogous manner to that described in the last paragraph of Example 7.

EXAMPLE 36

237 mg of methyl 6-(6-cyano-3,4-dihydro-2,2-dimethyl-2H-1-benzopyran-4-yl)-3-pyridinecarboxylate were dissolved in 30 ml of dichloromethane and 180 mg of m-chloroperbenzoic acid were added. The mixture was stirred at room temperature overnight and then washed in succession with sodium bisulphite solution, sodium bicarbonate solution and water, dried over sodium sulphate and evaporated. The resulting oil was triturated with diethyl ether to give a solid which was recrystallized from t-butyl methyl ether. There were obtained 60 mg of 2-(6-cyano-3,4-dihydro-2,2-dimethyl-2H-1-benzopyran-4-yl)-5-(methoxycarbonyl)pyridine N-oxide of melting point 135°–137° C.

The methyl 6-(6-cyano-3,4-dihydro-2,2-dimethyl-2H-1-benzopyran-4-yl)-3-pyridinecarboxylate used as the starting material was prepared as follows:

(A) 11 g of 2-iodopyridine-5-carboxylic acid were suspended in 300 ml of dichloromethane and 4.8 g of benzyl alcohol, 10 % of dicyclohexylcarbodiimide and 100 mg of 4-dimethylaminopyridine were added. The mixture was stirred at room temperature and, after 2 hours, filtered. The filtrate was evaporated and the residue was chromatographed on silica gel using firstly ethyl acetate/petroleum ether (1:9) and then ethyl acetate/petroleum ether (1:6) for the elution. There were obtained 12.2 g of benzyl 2-iodopyridine-5-carboxylate which was used without further purification.

(B) 12.2 g of benzyl 2-iodopyridine-5-carboxylate and 5.64 g of 4-(1,1-dimethyl-2-propynyloxy)benzonitrile were stirred with 32 mg of copper(I) iodide, 162 mg of triphenylphosphine and 180 mg of palladium(II) chloride in 280 ml of diethylamine at room temperature for 7 days under a nitrogen atmosphere. The mixture was evaporated and the residue was taken up in ethyl acetate and water. The organic phase was separated, dried over sodium sulphate and evaporated. The residue was chromatographed on silica gel using ethyl acetate/petroleum ether (1:4) for the elution. There were obtained 9.04 g of benzyl 2-[3-(4-cyanophenoxy)-3-methyl-1-butyn-1-yl]pyridine-5-carboxylate which was used without further purification.

(C) 9 g of benzyl 2-[3-(4-cyanophenoxy)-3-methyl-1-butyn-1-yl]pyridine-5-carboxylate were dissolved in 300 ml of 1,2-dichlorobenzene and the solution was added dropwise over a period of 5 hours to 10% ml of 1,2-dichlorobenzene heated at reflux. After a further 2 hours the mixture was allowed to cool to room temperature and was then evaporated. The residue was chromatographed on silica gel using ethyl acetate/petroleum ether (1:9), (1:6) and (1:4) for the elution. There were obtained 5.5 g of benzyl 6-(6-cyano-2,2-dimethyl-2H-1-benzopyran-4-yl)- 3-pyridinecarboxylate which was used without further purification.

(D) 5.06 g of benzyl 6-(6-cyano-2,2-dimethyl-2H-1-benzopyran-4-yl)-3-pyridinecarboxylate were heated at 100° C. with 7.8 ml of tributylamine, 244 mg of 10% palladium-on-charcoal and 0.9 ml of formic acid. After 12 hours a further 7.8 ml of tributylamine and 10 ml of formic acid were added. After 24 hours a further 2 ml of tributylamine and 3 ml formic acid were added. After 26 hours a further 170 mg of 10% palladium-on-charcoal, 2 ml tributylamine and 3 ml of formic acid were added. After 28 hours the mixture was evaporated and filtered. The filtrate was evaporated and the residue obtained was chromatographed on silica gel using ethyl acetate/petroleum ether (1:2) and ethyl acetate for the elution. There were obtained 1.4 g of 6-(6-cyano-2,2-dimethyl-2H-1-benzopyran-4-yl)-3-pyridinecarboxylic acid which was used without further purification.

(E) 1.4 g of 6-(6-cyano-2,2-dimethyl-2H-1-benzopyran-4-yl)-3-pyridinecarboxylic acid were dissolved in 200 ml of ethyl acetate and shaken under a hydrogen atmosphere overnight with 103 mg of 10% palladium-on-charcoal. The mixture was filtered and the filtrate was evaporated. There were obtained 680 mg of 6-(6-cyano-3,4-dihydro-2,2-dimethyl-2H-1-benzopyran-4-yl)-3-pyridinecarboxylic acid which was used without further purification.

(F) 300 mg of 6-(6-cyano-3,4-dihydro-2,2-dimethyl-2H-1-benzopyran-4-yl)-3-pyridinecarboxylic acid in 10 ml of methanol were treated with an ethereal solution of diazomethane until the yellow colour persisted. The yellow colour was discharged by the dropwise addition of acetic acid and the mixture was then evaporated. The residue was dissolved in ethyl acetate and the solution was washed with sodium bicarbonate solution, dried over sodium sulphate and evaporated to give, after recrystallization from t-butyl methyl ether, 270 mg of methyl 6-(6-cyano-3,4-dihydro-2,2-dimethyl-2H-1-benzopyran-4-yl)-3pyridinecarboxylate of melting point 131°–133° C.

EXAMPLE 37

1 g of 4-(5-amino-2-pyridyl)-2,2-dimethyl-2H-1-benzopyran-6-carbonitrile was dissolved in 15 ml of dichloromethane and 1 g of m-chloroperbenzoic acid was added. After stirring at room temperature for 1 hour a further 0.5 g of m-chloroperbenzoic acid was added. After stirring at room temperature overnight the mixture was washed in succession with sodium bisulphite solution, sodium bicarbonate solution and water, dried over sodium sulphate and evaporated. The residue was chromatographed on silica gel using firstly 10% (v/v) methanol/ethyl acetate and then 20% (v/v) methanol/ethyl acetate for the elution. The product, 5-amino-2-(6-cyano-2,2-dimethyl-2H-1-benzopyran-4-yl)-pyridine, was converted into the hydrochloride salt which was recrystallized from isopropanol. There were obtained 238 mg of 5-amino-2-(6-cyano-2,2-dimethyl-2H-1-benzopyran-4-yl)pyridine N-oxide hydrochloride of melting point 235°–237° C.

The 4-(5-amino-2-pyridyl)-2,2-dimethyl-2H-1-benzopyran-6-carbonitrile used as the starting material was prepared as follows:

(A) 2,2-Dimethyl-4-(5-nitro-2-pyridyl)-2H-1-benzopyran-6-carbonitrile was prepared from 4-(1,1-dimethyl-2propynyloxy)benzonitrile and 2-iodo-5-nitropyridine in an analogous manner to that described in Example 6(A).

(B) 1.91 g of 2,2-dimethyl-4-(5-nitro-2-pyridyl)-2H-1-benzopyran-6-carbonitrile were dissolved in 25 ml of acetic acid and 25 ml of water and 1.3 g of iron powder were added. After stirring at 100° C. for 1 hour the mixture was poured into 2M sodium hydroxide solution and the resulting mixture was extracted with ethyl acetate. The organic phase was filtered and the filtrate was dried over sodium sulphate and evaporated to give, after trituration with diethyl ether, 600 mg of 4-(5-amino-2-pyridyl)-2,2-dimethyl-2H-1-benzopyran-6-carbonitrile which was used without further purification.

EXAMPLE 38

In an analogous manner to that described in the first paragraph of Example 7, from 4-(5-amino-2-pyridyl)-3,4-dihydro-2,2-dimethyl-2H-1-benzopyran-6-carbonitrile there was obtained 5-amino-2-(6-cyano-3,4-dihydro-2,2-dimethyl-2H-1-benzopyran-4-yl)pyridine N-oxide of melting point 218°–220° C. (from acetonitrile).

The 4-(5-amino-2-pyridyl)-3,4-dihydro-2,2-dimethyl-2H-1-benzopyran-6-carbonitrile used as the starting material was prepared from 2,2-dimethyl-4-(5-nitro-2-pyridyl)-2H-1-benzopyran-6-carbonitrile in an analogous manner to that described in the last paragraph of Example 7.

EXAMPLE 39

400 mg of 4-(5-hydroxy-2-pyridyl)-2,2-dimethyl-2H-1-benzopyran-6-carbonitrile and 350 mg of m-chloroperbenzoic acid were stirred overnight in 100 ml of dichloromethane. The mixture was washed in succession with sodium bisulphite solution, sodium bicarbonate solution and water, dried over sodium sulphate and evaporated. The residue was chromatographed on silica gel using 10% (v/v) methanol/ethyl acetate for the elution. There were obtained 30 mg of 2-(6-cyano-2,2-dimethyl-2H-1-benzopyran-4-yl)-5-hydroxypyridine N-oxide of melting point 260°–262° C. (from ethanol).

The 4-(5-hydroxy-2-pyridyl)-2,2-dimethyl-2H-1-benzopyran-6-carbonitrile used as the starting material was prepared as follows:

1.62 g of 4-(5-amino-2-pyridyl)-2,2-dimethyl-2H-1-benzopyran-6-carbonitrile were suspended in 12 ml of concentrated hydrochloric acid, 30 g of ice and 18 ml of N-methylpyrrolidone. The mixture was cooled to $-5°$ C. and 0.44 g of sodium nitrite in 5 ml of water was added dropwise while maintaining the temperature below 0° C. After completion of the addition the mixture was allowed to warm to room temperature and was then heated at 40° C. for 1 hour. The mixture was extracted with ethyl acetate and the extract was evaporated. The residue was taken up in diethyl ether and water and the separated organic phase was washed with water, dried over sodium sulphate and evaporated. The residue was chromatographed on silica gel using ethyl acetate/petroleum ether (1:1) and ethyl acetate for the elution to give 270 mg of 4-(5-chloro-2-pyridyl)-2,2-dimethyl-2H-1-benzopyran-6-carbonitrile and 254 mg of 4-(5-hydroxy-2-pyridyl)-2,2-dimethyl-2H-1-benzopyran-6-carbonitrile.

EXAMPLE 40

In an analogous manner to that described in the first paragraph of Example 39, from 4-(5-chloro-2-pyridyl)-2,2-dimethyl-2H-1-benzopyran-6-carbonitrile there was obtained 5-chloro-2-(6-cyano-2,2-dimethyl-2H-1-benzopyran-4-yl)pyridine N-oxide in the form of an oil. NMR (300 MHz, CDCl$_3$): $\delta$8.30 (1H, broad s), 7.35 (1H, dd, 10Hz, 2Hz), 7.29 (1H, dd, 9Hz, 2Hz), 7.22 (1H, d, 10Hz), 6.87 (1H, d, 2Hz), 6.83 (1H, d, 10Hz), 5.82 (1H, s), 1.47 (6H, s). MS (EI): 3.12 (H$^+$[Cl$^{35}$]).

EXAMPLE 41

In an analogous manner to that described in the first paragraph of Example 39, from 4-(5-chloro-2-pyridyl)-3,4-dihydro-2,2-dimethyl-2H-1-benzopyran-6-carbonitrile there was obtained 5-chloro-2-(6-cyano-3,4-dihydro-2,2-dimethyl-2H-1-benzopyran-4-yl)pyridine N-oxide of melting point 159°–161° C. (from ethanol).

The 4-(5-chloro-2-pyridyl)-3,4-dihydro-2,2-dimethyl-2H-1-benzopyran-6-carbonitrile used as the starting material was prepared by catalytically hydrogenating 2,2-dimethyl-4-(5-nitro-2-pyridyl)-2H-1-benzopyran-6- carbonitrile in an analogous manner to that described in the last paragraph of Example 7 and then subjecting the resulting 4-(5-amino-2-pyridyl)-3,4-dihydro-2,2-dimethyl-2H-1-benzopyran-6-carbonitrile to the procedure described in the last paragraph of Example 39.

EXAMPLE 42

In an analogous manner to that described in the first paragraph of Example 6, from 2,2-dimethyl-4-(5-phenyl-2-pyridyl)-2H-1-benzopyran-6-carbonitrile there was obtained 2-(6-cyano-2,2-dimethyl-2H-1-benzopyran-4-yl)-5-phenylpyridine N-oxide of melting point 173°–175° C. (from ethyl acetate).

The 2,2-dimethyl-4-(5-phenyl-2-pyridyl)-2H-1-benzopyran-6-carbonitrile used as the starting material was prepared as follows: (A) 15.98 g of 2-chloro-5-phenylpyridine were dissolved in 150 ml of 55% aqueous hydroiodic acid and the solution was heated at reflux for 2 hours. Upon cooling a solid precipitated and this was filtered off and washed with water. The solid was partitioned between diethyl ether and 2M sodium hydroxide solution, and the organic phase was dried over sodium sulphate and evaporated to give 15.87 g of 2-iodo-5-phenylpyridine which was used without further purification. (B) In an analogous manner to that described in Example 6 (A) and (B), from 2-iodo-5-phenylpyridine and 4-(1,1-dimethyl-2-propynyloxy)benzonitrile there was obtained 2,2-dimethyl-4-(5-phenyl-2-pyridyl)-2H-1-benzopyran -6-carbonitrile.

EXAMPLE 43

In an analogous manner to that described in the first paragraph of Example 7, from 3,4-dihydro-2,2-dimethyl-4-(5-phenyl-2-pyridyl)-2H-1-benzopyran-6-carbonitrile there was obtained 2-(6-cyano-3,4-dihydro-2,2-dimethyl-2H-1-benzopyran-4-yl)-5-phenylpyridine N-oxide of melting point 174°–176° C. (from ethyl acetate).

The 3,4-dihydro-2,2-dimethyl-4-(5-phenyl-2-pyridyl)-2H-1-benzopyran-6-carbonitrile used as the starting material was prepared by catalytically hydrogenating 2,2-dimethyl-4-(5-phenyl-2-pyridyl)-2H-1-benzopyran6-carbonitrile in an analogous manner to that described in the last paragraph of Example 7.

EXAMPLE 44

In an analogous manner to that described in the first paragraph of Example 3, from 6-acetyl-2,2-dimethyl-4-(2-pyridyl)-2H-1-benzopyran there was obtained 2-(6-acetyl-2,2-dimethyl-2H-1-benzopyran-4-yl)pyridine N-oxide of melting point 165°–167° C. (from diethyl ether).

The 6-acetyl-2,2-dimethyl-4-(2-pyridyl)-2H-1-benzopyran used as the starting material was prepared from 2,2-dimethyl-4-(2-pyridyl)-2H-1-benzopyran in an analogous manner to that described in the last paragraph of Example 3.

EXAMPLE 45

In an analogous manner to that described in the first paragraph of Example 6, from 6-bromo-2,2-dimethyl-4-(2-pyridyl)-2H-1-benzopyran there was obtained 2-(6-bromo-2,2-dimethyl-2H-1-benzopyran-4-yl)pyridine N-oxide of melting point 146°–148° C. (from ethyl acetate).

The 6-bromo-2,2-dimethyl-4-(2-pyridyl)-2H-1-benzopyran used as the starting material was prepared as follows: (A) 69.2 g of p-bromophenol and 33.6 g of 2-methylbut-3-yn-2-ol were dissolved in 600 ml of dichloromethane and 75 ml of diethyl azodicarboxylate were added. 126 g of triphenylphosphine were added portionwise and the mixture was stirred overnight. The mixture was washed with dilute hydrochloric acid and 2M sodium hydroxide solution, dried over sodium sulphate and evaporated. The residue was chromatographed on silica gel using ethyl acetate/petroleum ether (1:10) for the elution. There was obtained an oil which was distilled to give 14.4 g of 4-(1,1-dimethyl-2-propynyloxy)bromobenzene of boiling point 96°–106° C./1 mmHg. (B) In an analogous manner to that described in Example 6(A), from 4-(1,1-dimethyl-2-propynyloxy)bromobenzene and 2-iodopyridine there was obtained 6-bromo-2,2-dimethyl-4-(2-pyridyl)-2H-1-benzopyran.

EXAMPLE 46

In an analogous manner to that described in the first paragraph of Example 6, from 4-[5-(4-methylphenyl)-2pyridyl]-2,2-dimethyl-2H-1-benzopyran-6-carbonitrile there was obtained 2-(6-cyano-2,2-dimethyl-2H-1-benzopyran-4-yl)-5-(4-methylphenyl)pyridine N-oxide of melting point 173°–175° C. (decomposition) (from ethyl acetate).

The 4-[5-(4-methylphenyl)-2-pyridyl]-2,2-dimethyl-2H-1-benzopyran-6-carbonitrile used as the starting material was prepared as follows: (A) 9.5 g of 4-(5-amino-2-pyridyl)-2,2-dimethyl-2H-1-benzopyran-6-carbonitrile were dissolved in 150 ml of acetic acid and 100 ml of water. 3.16 g of sodium nitrite in 10 ml of water were added at such a rate as to keep the temperature below 5° C. After 15 minutes 23 g of potassium iodide in 20 ml of water were added and the mixture was stirred at room temperature for 1 hour. The mixture was then poured into 1.1 of 2M sodium hyroxide solution and extracted with ethyl acetate. The organic extract was dried over sodium sulphate and evaporated. The residue was chromatographed on silica gel using ethyl acetate/petroleum ether (1:4) for the elution to give 4.78 g of 4-(5-iodo-2-pyridyl)-2,2-dimethyl-2H-1-benzopyran-6-carbonitrile which was used without further purification. (B) 440 mg of 4-(5-iodo-2-pyridyl)-2,2-dimethyl-2H-1-benzopyran-6-carbonitrile, 386 mg of p-tolyltrimethyltin, 440 mg of lithium chloride and 16 mg of bis(triphenylphosphine)palladium dichloride in 4 ml of dimethylformamide were heated at 100° C. for 2 hours. After cooling to room temperature 10% aqueous ammonia and ethyl acetate were added, the phases were separated and the aqueous phase was back-extracted with ethyl acetate. The combined organic phases were dried over sodium sulphate and evaporated. The residue was chromatographed on silica gel using ethyl acetate/petroleum ether (1:4) for the elution to give 268 mg of 4-[5-(4-methylphenyl)-2-pyridyl]-2,2-dimethyl-2H-1-benzopyran-6-carbonitrile which was used without further purification.

EXAMPLE 47

In an analogous manner to that described in the first paragraph of Example 4, from 6-acetyl-2-methyl-2-phenyl-4-(2-pyridyl)-2H-1-benzopyran there was obtained 2-(6-acetyl-2-methyl-2-phenyl-2H-1-benzopyran-4-yl)pyridine N-oxide of melting point 192°–194° C. (from acetonitrile). The 6-acetyl-2-methyl-2-phenyl-4-(2-pyridyl)-2H-1-benzopyran used as the starting material was prepared from 2-methoxyphenyl 2-pyridyl ketone and 1-bromo-2-phenyl-1-propene in an analogous manner to that described in Example 4(B)–(D) and (F).

EXAMPLE 48

In an analogous manner to that described in the first paragraph of Example 7, from (−)-3,4-dihydro-2,2-dimethyl-4-(2-pyridyl)-2H-1-benzopyran-6-carbonitrile there was obtained (−)-2-(6-cyano-3,4-dihydro-2,2-dimethyl-2H-1-benzopyran-4-yl)pyridine N-oxide of melting point 142°–144° C. (from diethyl ether); $[\alpha]^{20}_{589} = -76.8°$ (c=0.997 in ethanol).

The (−)-3,4-dihydro-2,2-dimethyl-4-(2-pyridyl)-2H-1-benzopyran-6-carbonitrile used as the starting material was prepared as follows: (A) 36.15 g of 3,4-dihydro-2,2-dimethyl-4-(2-pyridyl)-2H-1-benzopyran-6-carboxylic acid and 41.39 g of quinine were dissolved in 650 ml of ethyl acetate and left to crystallize. 16.5 g of solid were filtered off and dissolved in 250 ml of ethyl acetate and 150 ml of 2M acetic acid. The organic phase was washed with 2M acetic acid. The combined aqueous phases were washed with ethyl acetate and the organic phase was washed with 25 ml of 2% (w/v) citric acid solution. The organic phases were combined, washed with water, dried over sodium sulphate and evaporated to give 7.2 g of (−)-3,4-dihydro-2,2-dimethyl-4-(2-pyridyl)-2H-1-benzopyran-6-carboxylic acid. (B) 7.2 g of (-)-3,4-dihydro-2,2-dimethyl-4-(2-pyridyl)-2H-1-benzopyran-6-carboxylic acid were heated at 70° C. in 30 ml of thionyl chloride for 1 hour and the mixture was then evaporated. The residue was dissolved in toluene and the solution was evaporated in order to remove traces of thionyl chloride. The residue was dissolved in 100 ml of dichloromethane and 50 ml of concentrated aqueous ammonia were added while stirring. Stirring was then continued for 15 minutes. The organic phase was separated, washed with water, dried over sodium sulphate and evaporated to give 7.1 g of (-)-3,4-dihydro-2,2-dimethyl-4-(2-pyridyl)-2H-1-benzopyran-6-carboxamide which was used without further purification. (C) 7.19 g of (−)-3,4-dihydro-2,2-dimethyl-4-(2-pyridyl)-2H-1-benzopyran-6-carboxamide were heated at 80° C. in 25 ml of phosphorus oxychloride for 30 minutes. The mixture was then cooled and evaporated. The residue was dissolved in dichloromethane and 2M sodium carbonate solution. The organic phase was separated, dried over sodium sulphate and evaporated to give 6.65 g of (−)-3,4-dihydro-2,2-dimethyl-4-(2-pyridyl)-2H-1-benzopyran-6-carbonitrile which was used without further purification.

EXAMPLE 49

In an analogous manner to that described in the first paragraph of Example 7, from (+)-3,4-dihydro-2,2-dimethyl-4-(2-pyridyl)-2H-1-benzopyran-6-carbonitrile there was obtained (+)-2-(6-cyano-3,4-dihydro-2,2-dimethyl-2H-1-benzopyran-4-yl)pyridine N-oxide of melting point 143°–144° C. (from diethyl ether); $[\alpha]^{20}_{589} = 78.8°$ (c=1.001 in ethanol).

The (+)-3,4-dihydro-2,2-dimethyl-4-(2-pyridyl)-2H-1-benzopyran-6-carbonitrile used as the starting material was prepared from the mother liquors from the quinine resolution described in Example 48(A). The free acid was prepared in an analogous manner. 4.01 g of this acid were dissolved in 90 ml of acetone and 2.42 g of (S)-(−)-1-(1-naphthyl)ethylamine were added. A solid crystallized out and was filtered off and recrystallized from dioxan. The crystals were dissolved in ethyl acetate and 2% (w/v) citric acid. The separated aqueous phase was backextracted with ethyl acetate, the organic phases were combined, washed with water, dried over sodium sulphate and evaporated to give 1.41 g of (+)-3,4-dihydro-2,2-dimethyl-4-(2-pyridyl)-2H-1-benzopyran-6-carboxylic acid. This acid was converted into (+)-3,4-dihydro-2,2-dimethyl-4-(2-pyridyl)-2H-1-benzopyran-6-carbonitrile in an analogous manner to that described in Example 48(B) and (C).

EXAMPLE 50

2.24 g of 5-benzyloxy-2-[3-(4-cyanophenoxy)-3-methyl-1-butenyl]pyridine N-oxide in 45 ml of toluene were heated to 80° C. for 12 hours. The solvent was removed by evaporation and the residue was chromatographed on silica gel using diethyl ether/methanol (97.5:2.5) for the elution to give 0.45 g of 5-benzyloxy-2-(6-cyano-3,4-dihydro-2,2-dimethyl-2H-1-benzopyran-4-yl)pyridine N-oxide in the form of a white solid of melting point 224° C.

The 5-benzyloxy-2-[3-(4-cyanophenoxy)-3-methyl-1-butenyl]pyridine N-oxide used as the starting material was prepared as follows: (A) 23.8 g of 4-cyanophenol in 150 ml of dimethylformamide were added dropwise to a stirred suspension of 6 g of 80% sodium hydride in 100 ml of dimethylformamide and the mixture was then stirred for a further 1 hour. 39 g of ethyl bromoisobutyrate were added dropwise and the mixture was heated to 100° C. for 76 hours. The solvents were removed by evaporation and the residue was partitioned between diethyl ether and water. The organic phase was washed in succession with 2M sodium hydroxide solution and sodium chloride solution and then evaporated to give 9.4 g of ethyl 2-(4-cyanophenoxy)-2-methylpropionate in the form of a colourless viscous liquid of boiling point 115°–117° C./0.05 mmHg. (B) 5 ml of a 1.2M solution of butyllithium in n-hexane were added to a solution of 0.6 g of diisopropylamine in 10 ml of tetrahydrofuran while stirring at −78° C. under a nitrogen atmosphere. The solution was stirred for a further 15 minutes and then 1.07 g of 5-benzyloxy-2-methylpyridine N-oxide in 10 ml of tetrahydrofuran were added. The mixture was allowed to warm to 20° C, stirred for 30 minutes and then cooled to −78° C. 1.16 g of ethyl 2-(4-cyanophenoxy)-2-methylpropionate were added and the mixture was then allowed to warm to 20° C. and was stirred for 16 hours. The mixture was diluted with 50 ml of ethyl acetate and washed in succession with water and sodium chloride solution. The organic phase was evaporated and the residue was chromatographed on silica gel using dichloromethane/methanol (94:4) for the elution to give 0.46 g of 5-benzyloxy-2-[3-(4-cyanophenoxy)-3-methyl-2-oxobutyl]pyridine N-oxide in the form of a Pale yellow solid of melting point 134°–136° C. (from diethyl ether). (C) 0.46 g of sodium borohydride was added to a stirred solution of 4.53 g of 5-benzyloxy-2-[3-(4-cyanophenoxy)-3-methyl-2-oxobutyl]pyridine N-oxide in 60 ml of ethanol. After 2 hours the solution was diluted with 200 ml of water and extracted with diethyl ether. The organic phase was evaporated to give 3.67 g of 5-benzyloxy-2-[3-(4-cyanophenoxy)-2-hydroxy-3-methylbutyl]pyridine N-oxide of melting point 125° C. after recrystallization from ethanol. (D) 0.7 g of methanesulphonyl chloride was added to a stirred solution of 2.3 g of 5-benzyloxy-2-[3-(4-cyanophenoxy)-2-hydroxy-3-methylbutyl]pyridine N-oxide and 1 ml of 2,6-lutidine in 10 ml of dichloromethane. The mixture was stirred for 4.5 hours and then a further 1 ml of 2,6-lutidine and 0.7 g of methanesulphonyl chloride were added. After 2.5 hours a further 1 ml of 2,6-lutidine and 0.7 g of methanesulphonyl chloride were added and the mixture was stirred for 16 hours. The mixture was then diluted with 50 ml of dichloromethane and washed in succession with 2M hydrochloric acid, water and 10% sodium bicarbonate solution. The organic solution was evaporated and the residue was chromatographed on silica gel using diethyl ether/methanol (9:1) for the elution to give 0.89 g of 5-benzyloxy-2-[3-(4-cyanophenoxy)-3-methyl-2(methylsulphonyloxy)butyl]pyridine N-oxide in the form of a cream solid of melting point 142° C. after recrystallization from ethyl acetate. (E) 1.69 g of 5-benzyloxy-2-[3-(4-Cyanophenoxy)-3-methyl-2-(methylsulphonyloxy)-butyl]pyridine N-oxide were added to a solution of 0.14 g of 80% sodium hydride in 15 ml of isopropanol and the solution was stirred at 20° C. for 16 hours. The solvent was then removed by evaporation and the residue was partitioned between ethyl acetate and sodium chloride solution. The organic phase was washed with sodium chloride solution and then evaporated to give 1.64 g of 5-benzyloxy-2-[3-(4-cyanophenoxy)-3-methyl-1-butenyl]pyridine N-oxide in the form of a pale cream solid of melting point 125° C. after recrystallization from ethyl acetate.

EXAMPLE 51

0.21 g of 5-benzyloxy-2-(6-cyano-3,4-dihydro-2,2-dimethyl-2H-1-benzopyran-4-yl)pyridine N-oxide in 90 ml of methanol was hydrogenated over 10% palladium-on-carbon at room temperature and under atmospheric pressure for 30 minutes. The catalyst was removed by filtration and the filtrate was evaporated. The residue was chromatographed on silica gel using dichloromethane/methanol (19:1) for the elution to give 0.05 g of 2-(6-cyano-3,4-dihydro-2,2-dimethyl-2H-1-benzopyran-4-yl)-5-hydroxypyridine N-oxide in the form of an off-white solid of melting point 224° C (from ethyl acetate).

EXAMPLE 52

In an analogous manner to that described in the first paragraph of Example 7, from rac-trans-3,4-dihydro-3-hydroxy-2,2-dimethyl-4-(2-pyridyl)-2H-1-benzopyran-6carbonitrile there was obtained rac-trans-2-(6-cyano-3,4-dihydro-3-hydroxy-2,2-dimethyl-2H-1-benzopyran-4-yl)pyridine N-oxide of melting point 222°-224° C. (from acetonitrile).

The rac-trans-3,4-dihydro-3-hydroxy-2,2-dimethyl-4-(2-pyridyl)-2H-1-benzopyran-6-carbonitrile used as the starting material was prepared as follows: (A) 3 g of 2,2-dimethyl-4-(2-pyridyl)-2H-1-benzopyran-6-carbonitrile and 420 mg of sodium tungstate were heated in 30 ml of methanol and 30 ml of acetonitrile at 50° C. and 2 ml of 30% (w/v) hydrogen peroxide were added. After heating overnight the mixture was evaporated and the residue was taken up in dichloromethane and water. The organic phase was separated, dried over sodium sulphate and evaporated. The residue was chromatographed on silica gel using ethyl acetate/petroleum ether (1:3 and 1:2) for the elution to give 440 mg of la,7b-dihydro-2,2-dimethyl-7b-(2-pyridyl)-2H-oxireno[c][1]benzopyran-6-carbonitrile which was used without further purification. (B) 646 mg of la,7b-dihydro-2,2-dimethyl-7b-(2-pyridyl)-2H-oxireno[c][1]benzopyran-6-carbonitrile were dissolved in 100 ml of ethanol and 100 mg of 10% palladium-on-charcoal were added. The mixture was shaken under a hydrogen atmosphere overnight and then filtered. The filtrate was evaporated and the resulting oil was chromatographed twice on silica gel, with the elution being carried out initially using ethyl acetate/petroleum ether (1:3) and then 1% to 2% (v/v) methanol/dichloromethane. There were obtained 66 mg of rac-cis-3,4-dihydro-3-hydroxy-2,2-dimethyl-4-(2-pyridyl)-2H-1-benzopyran-6-carbonitrile of melting point 186°-188° C. (from acetonitrile) and 340 mg of rac-trans-3,4-dihydro-3-hydroxy-2,2-dimethyl-4-(2-pyridyl)-2H-1-benzopyran-6carbonitrile of melting point 175°-176° C. (from t-butyl methyl ether).

EXAMPLE 53

In an analogous manner to that described in the first paragraph of Example 7, from rac-cis-3,4-dihydro-3-hydroxy-2,2-dimethyl-4-(2-pyridyl)-2H-1-benzopyran-6carbonitrile there was obtained rac-cis-2-(6-cyano-3,4-dihydro-3-hydroxy-2,2-dimethyl -2H-1-benzopyran-4-yl)pyridine N-oxide of melting point 215°-216° C. (from acetonitrile).

EXAMPLE 54

242 mg of 3,4-dihydro-2,2-dimethyl-4-(2-pyrimidinyl)-2H-1-benzopyran-6-carbonitrile were dissolved in 5 ml of dichloromethane at room temperature and 450 mg of m-chloroperbenzoic acid were added. After stirring overnight the mixture was washed with sodium bisulphite solution and sodium bicarbonate solution. The organic phase was dried over sodium sulphate and evaporated. The residue was chromatographed on silica gel using ethyl acetate/ethanol/formic acid (40:4:1) for the elution. The product was obtained in the form of an oil which was dissolved in diethyl ether and washed with sodium bicarbonate solution. The organic phase was dried over sodium sulphate and evaporated. The resulting oil was crystallized from t-butyl methyl ether to give 25 mg of 2-(6-cyano-3,4-dihydro-2,2-dimethyl-2H-1-benzopyran-4-yl)pyrimidine 1-oxide of melting point 98°-100° C.

The 3,4-dihydro-2,2-dimethyl-4-(2-pyrimidinyl)-2H-1-benzopyran-6-carbonitrile used as the starting material was prepared as follows: (A) 0.63 g of 4-(1,1-dimethyl-2-propynyloxy)benzonitrile, 0.75 g of 2-iodopyrimidine, 18 mg of triphenylphosphine, 12 mg of palladium(II) chloride and 3.5 mg of copper(I) iodide were stirred overnight in 20 ml of triethylamine under nitrogen. The mixture was evaporated to dryness and then ethyl acetate and water were added. The organic phase was dried over sodium sulphate and evaporated. The residue was chromatographed on silica gel using ethyl acetate/petroleum ether (1:3) and subsequently ethyl acetate/petroleum ether (1:1) for the elution. There were obtained 580 mg of 4-[1,1-dimethyl-3-(2-pyrimidinyl)-2-propynyloxy]benzonitrile as an oil. (B) 580 mg of 4-[1,1-dimethyl-3-(2-pyrimidinyl)-2-propynyloxy]benzonitrile were heated at reflux for 3 hours in 20 ml of dichlorobenzene. The solution was allowed to cool and was then evaporated to dryness. The residue was chromatographed on silica gel using ethyl acetate/petroleum ether (1:2) and subsequently ethyl acetate/petroleum ether (1:1) for the elution. There was obtained 361 mg of 2,2-dimethyl-4-(2-pyrimidinyl)-2H-1-benzopyran-6-carbonitrile which melted at 108°-109.5° C. after recrystallization from tert-butyl methyl ether. (C) 1.0 g of 2,2-dimethyl-4-(2-pyrimidinyl)-2H-1-benzopyran-6-carbonitrile was dissolved in 100 ml of ethanol, added to 10% palladium-on-charcoal and shaken under an atmosphere of hydrogen at room temperature. After 2 hours the catalyst was filtered off and the filtrate was evaporated. The residue was chromatographed on silica gel using ethyl acetate/petroleum ether (1:1) for the elution. The product was recrystallized from cyclohexane to give 0.5 g of 3,4-dihydro-2,2-dimethyl-4-(2-pyrimidinyl)-2H-1-benzopyran-6-carbonitrile of melting point 109°–111° C.

EXAMPLE 55

In an analogous manner to that described in the first paragraph of Example 8, from 0.22 g of 6-[5-cyano-2-hydroxy-α-(2-methylpropenyl)benzyl]pyrimidine 1-oxide there was obtained 0.01 g of 6-(6-cyano-3,4-dihydro-2,2-dimethyl-2H-1-benzopyran-4-yl)pyrimidine 1-oxide in the form of an off-white solid (from ethyl acetate/n-hexane).

Analysis for $C_{16}H_{15}N_3O_2$: Calculated: C: 68.31; H: 5.37; N: 14.94%; Found: C: 68.01; H: 5.35; N: 14.71%.

The 6-[5-cyano-2-hydroxy-α-(2-methylpropenyl)benzyl]pyrimidine 1-oxide used as the starting material was prepared as follows: (A) 10 ml of a 1.2M solution of butyllithium in n-hexane were added to a solution of 1.68 ml of diisopropylamine in 50 ml of tetrahydrofuran while stirring at −78° C. under a nitrogen atmosphere. The solution was stirred for a further 15 minutes and a solution of 4-methylpyrimidine in 20 ml of tetrahydrofuran was then added. The solution was allowed to warm to 20° C. and was stirred for 2 hours. The solution was then cooled to −78° C, 2.33 g of ethyl 2-(4-cyanophenoxy)-2-methylpropionate in 30 ml of tetrahydrofuran were added and the mixture was allowed to warm to 20° C. and was stirred for 16 hours. The mixture was then partitioned between ethyl acetate and water. The organic phase was washed with sodium chloride solution and evaporated. The residue was chromatographed on silica gel using ethyl acetate for the elution to give 0.69 g of 4-[2- hydroxy-1,1-dimethyl-3-(4-pyrimidinyl)-2-propenyloxy]benzonitrile in the form of a yellow solid of melting point 115°–117° C. (from ethyl acetate/n-hexane). (B) 0.013 mg of sodium borohydride was added to a solution of 0.098 mg of 4-[2-hydroxy-1,1-dimethyl-3-(4-pyrimidinyl)-2-propenyloxy]benzonitrile in 3 ml of ethanol and the solution was stirred at 20° C. for 16 hours. The solvent was removed by evaporation and the residue was partitioned between ethyl acetate and water. The organic phase was evaporated and the residue was chromatographed on silica gel using ethyl acetate for the elution. There was obtained 0.073 g of 4-[2-hydroxy-1,1-dimethyl-3-(4-pyrimidinyl)propoxy]benzonitrile in the form of a white solid of melting point 96°–98° C. (C) 3.77 g of m-chloroperbenzoic acid were added to a solution of 4.78 g of 4-[2-hydroxy-1,1-dimethyl-3-(4-pyrimidinyl)propoxy]benzonitrile in 75 ml of dichloromethane and the mixture was stirred at 20° C. for 16 hours. A further 0.38 g of m-chloroperbenzoic acid was added and the mixture was stirred at 20° C. for 24 hours. The mixture was then washed in succession with water and sodium chloride solution. The organic solution was evaporated and the residue was chromatographed on silica gel using diethyl ether/methanol (9:1) for the elution to give 0.98 g of 6-[3-(4-cyanophenoxy)-2-hydroxy-3-methylbutyl]pyrimidine 1-oxide in the form of a white solid of melting point 105°–107.5° C. (from ethyl acetate). (D) 0.23 g of methanesulphonyl chloride was added to a solution of 0.59 g of 6-[3-(4-cyanophenoxy)-2-hydroxy-3-methylbutyl]pyrimidine 1-oxide and 0.2 g of triethylamine in 10 ml of dichloromethane. The mixture was stirred at 20° C. for 2 hours and then a further 0.46 g of methanesulphonyl chloride and 0.4 g of triethylamine were added. After 2 hours a further 0.6 g of triethylamine was added and the mixture was stirred for 1.5 hours. The mixture was then washed with water and evaporated. The residue was chromatographed on silica gel using ethyl acetate for the elution to give 0.25 g of (E)-6-[3-(4-cyanophenoxy)-3-methyl-1-butenyl]pyrimidine 1-oxide in the form of a pale yellow solid of melting point 101°–102° C. (E) 0.24 g of (E)-6-[3-(4-cyanophenoxy)-3-methyl-1-butenyl]pyrimidine 1-oxide in 30 ml of toluene was heated to reflux for 16 hours. The solvent was then removed by evaporation and the residue was chromatographed on silica gel using ethyl acetate for the elution. There was obtained 0.08 g of 6-[5-cyano-2-hydroxy-α-(2-methylpropenyl)benzyl]pyrimidine 1-oxide in the form of a white solid of melting point 190°–192° C. (from ethyl acetate).

EXAMPLE 56

In an analogous manner to that described in the first paragraph of Example 8, from 0.35 g of 6-[5-cyano-2-hydroxy-α-(2-methylpropenyl)benzyl]pyrazine 1-oxide there was obtained 0.02 g of 2-(6-cyano-3,4-dihydro-2,2-dimethyl-2H-1-benzopyran-4-yl)pyrazine 1-oxide in the form of a white solid of melting point 166°–168° C. (from diethyl ether).

The 6-[5-cyano-2-hydroxy-α-(2-methylpropenyl)benzyl]pyrazine 1-oxide used as the starting material was prepared as follows: (A) 10 ml of a 1.2M solution of butyllithium in n-hexane were added to a solution of 1.68 ml of diisopropylamine in 10 ml of tetrahydrofuran while stirring at −78° C. under a nitrogen atmosphere The solution was stirred for a further 15 minutes and then 0.94 g of 2-methylpyrazine in 20 ml of tetrahydrofuran was added. The solution was allowed to warm to 20° C. and was stirred for 1 hour. The solution was then cooled to −78° C, 2.33 g of ethyl 2-(4-cyanophenoxy)-2-methylpropionate in 30 ml of tetrahydrofuran were added and the mixture was allowed to warm to 20° C. The mixture was treated with 20 ml of water and the solvent was removed by evaporation. The residue was chromatographed on silica gel using ethyl acetate for the elution to give 1.37 g of 4-[1,1-dimethyl-2-oxo-3-(2pyrazinyl)propoxy]benzonitrile. (B) 0.107 g of sodium borohydride was added to a stirred suspension of 0.79 g of 4-[1,1-dimethyl-2-oxo-3-(2-pyrazinyl)propoxy]benzonitrile in 20 ml of ethanol. The mixture was stirred at 20° C. for 1.5 hours and was then diluted with water. The solution was extracted with ethyl acetate and the organic phase was then washed with sodium chloride solution and evaporated to give 0.5 g of 4-[2-hydroxy-1,1-dimethyl-3-(2-pyrazinyl)propoxy]benzonitrile in the form of a white solid of melting point 94°–95° C. (from diethyl ether). (C) 0.18 g of m-chloroperbenzoic acid was added to a stirred solution of 0.28 g of 4-[2-hydroxy-1,1-dimethyl-3(2-pyrazinyl)propoxy]benzonitrile in 10 ml of dichloromethane. After 16 hours a further 36 mg of m-chloroperbenzoic acid were added and the mixture was stirred for 24 hours. The solvents were then removed by evaporation and the residue was chromatographed on silica gel using diethyl ether/methanol (95:5) for the elution to give 0.09 g of 2-[3-(4-cyanophenoxy)-2-hydroxy-3-methylbutyl]pyrazine 1-oxide in the form of a white solid of melting point 103°–104° C. (from diethyl ether). (D) 0.32 g of methanesulphonyl chloride was added to a stirred solution of 0.84 g of 2-[3-(4-cyanophenoxy)-2-hydroxy-3- methylbutyl]pyrazine 1-oxide in 5 ml of pyridine. The mixture was stirred at 20° C. for 5 hours and a further 0.32 g of methanesulphonyl chloride was then added. The mixture was stirred at 20° C. for 70 hours and then poured into 2M hydrochloric acid. The solution was extracted with dichloromethane and the organic phase was washed with sodium chloride solution and evaporated. The residue was triturated with n-hexane to give 0.95 g of 2-[2-(4-cyanophenoxy)-2-methyl-3-(methylsulphonyl)propyl]pyrazine 1-oxide in the form of a white solid of melting point 146°–147° C. (E) 0.89 g of 2-[2-(4-cyanophenoxy)-2-methyl-3-(methylsulphonyl)propyl]pyrazine 1-oxide was added to a solution of 71 mg of 80% sodium hydride in 5 ml of isopropanol and the mixture was stirred at 20° C. for 16 hours. The solvent o was removed by evaporation and the residue was partitioned between water and ethyl acetate. The organic solution was washed with sodium chloride solution and evaporated. The residue was chromatographed on silica gel using ethyl acetate/n-hexane (4:1) for the elution to give 0.5 g of (E)-2-[2-(4-cyanophenoxy)-2-methyl-1-butenyl]Pyrazine 1-oxide in the form of a white solid of melting point 107°–109° C. (F) 0.47 g of (E)-2-[2-(4-cyanophenoxy)-2-methyl-1-butenyl]pyrazine 1-oxide in 10 ml of toluene was heated to reflux for 16 hours. The cooled mixture was then filtered to give 0.4 g of 6-[5-cyano-2-hydroxy-α-(2methylpropenyl)benzyl]pyrazine 1-oxide in the form of a pale tan solid of melting point 212°–213° C.

EXAMPLE 57

450 mg of m-chloroperbenzoic acid were added at room temperature to a solution of 624 mg of 2,2-dimethyl-4-(2-quinolyl)-2H-1-benzopyran-6-carbonitrile in 20 ml of dichloromethane. After stirring at room temperature for 6 hours the mixture was washed with sodium bicarbonate solution and the organic phase was dried over sodium sulphate and evaporated. The residue was chromatographed on silica gel using ethyl acetate/petroleum ether (4:1) for the elution and then chromatographed on silica gel a second time using methanol/ethyl acetate (1:9) for the elution. The product was recrystallized from toluene to give 45 mg of 2-(6-cyano-2,2-dimethyl-2H-1-benzopyran-4-yl)quinoline 1-oxide of melting point 177° C.

The 2,2-dimethyl-4-(2-quinolyl)-2H-1-benzopyran-6-carbonitrile used as the starting material was prepared as follows: (A) 5.1 g of 2-iodoquinoline were added at room temperature to a solution of 18 mg of palladium(II) chloride, 52 mg of triphenylphosphine and 38 mg of copper(I) iodide in 100 ml of diethylamine. 3.7 g of 4-(1,1-dimethyl-2-propynyloxy)benzonitrile were added. After stirring at room temperature for 18 hours the mixture was evaporated and the residue was dissolved in ethyl acetate and water. The organic phase was dried over sodium sulphate and evaporated. The residue was chromatographed on silica gel using ethyl acetate/petroleum ether (1:2) for the elution to give 5.8 g of 4-[1,1-dimethyl-3-(2-quinolyl)-2-propynyloxy]benzonitrile as a yellow gum. (B) 5.8 g of 4-[1,1-dimethyl-3-(2-quinolyl)-2-propynyloxy]benzonitrile were heated at reflux for 2 hours in 50 ml of dichlorobenzene. The mixture was allowed to cool to room temperature and was then evaporated to dryness. The residue was chromatographed on silica gel using ethyl acetate/petroleum ether (1:3) for the elution. The product was recrystallized from isopropanol to give 2.1 g of 2,2-dimethyl-4-(2-quinolyl)-2H-1-benzopyran-6-carbonitrile of melting point 102°–104° C.

EXAMPLE 58

203 mg of m-chloroperbenzoic acid were added at room temperature to a solution of 314 mg of 3,4-dihydro-2,2-dimethyl-4-(2-quinolyl)-2H-1-benzopyran-6-carbonitrile in 10 ml of dichloromethane. After stirring for 2 hours the mixture was washed with sodium bisulphite solution and sodium bicarbonate solution. The organic phase was dried over sodium sulphate and evaporated. The residue was recrystallized from diethyl ether to give 230 mg of 2-(6-cyano-3,4-dihydro-2,2-dimethyl-2H-1-benzopyran-4-yl)quinoline 1-oxide of melting point 183°–185° C.

The 3,4-dihydro-2,2-dimethyl-4-(2-quinolyl)-2H-1-benzopyran-6-carbonitrile used as the starting material was prepared as follows:

624 mg of 2,2-dimethyl-4-(2-quinolyl)-2H-1-benzopyran-6-carbonitrile were shaken at room temperature under a hydrogen atmosphere in 25 ml of ethanol with 50 mg of 10% palladium-on-charcoal. After 4 hours the mixture was filtered and the filtrate was evaporated. The residue was chromatographed on silica gel using ethyl acetate/petroleum ether (1:2) for the elution. The product was recrystallized from isopropanol to give 410 mg of 3,4-dihydro-2,2-dimethyl-4-(2-quinolyl)-2H-1-benzopyran-6-carbonitrile of melting point 174°–176° C.

EXAMPLE 59

1.02 g of 4-(2-methoxyphenyl)-2,2-dimethyl-2H-1-benzopyran-6-carbonitrile and 736 mg of sodium methanethiolate were heated at reflux in 10 ml of dimethylformamide under a nitrogen atmosphere for 1.5 hours and then poured into a mixture of diethyl ether and water. The organic phase was separated, dried over sodium sulphate and evaporated. The residue was chromatographed on silica gel using petroleum ether/ethyl acetate (3:1) for the elution. The resulting solid was recrystallized from diethyl ether/petroleum ether to give 210 mg of 4-(2-hydroxyphenyl)-2,2-dimethyl-2H-1-benzopyran-6-carbonitrile of melting point 139°–140° C.

The 4-(2-methoxyphenyl)-2,2-dimethyl-2H-1-benzopyran-6-carbonitrile used as the starting material was prepared as follows: (A) 2.34 g of 2-iodoanisole were added at room temperature to a solution of 9 mg of palladium(II) chloride, 26 mg of o triphenylphosphine and 19 mg of copper(I) iodide in 25 ml of diethylamine. This mixture was treated with 1.85 g of 4-(1,1-dimethyl-2-propynyloxy)benzonitrile and the resulting mixture was stirred for 48 hours. The mixture was evaporated and the residue was dissolved in a mixture of ethyl acetate and water. The organic phase was separated, dried over sodium sulphate and evaporated. The residue was chromatographed on silica gel using ethyl acetate/petroleum ether (1:4) for the elution to give 0.99 g of 4-[1,1-dimethyl-3-(2-methoxyphenyl)-2-propynyloxy]benzonitrile in the form of an oil. (B) 0.99 g of 4-[1,1-dimethyl-3-(2-methoxyphenyl)-2-propynyloxy]benzonitrile was dissolved in 10 ml of 1,2-dichlorobenzene and heated at reflux for 1.5 hours. After cooling the solution was evaporated and the residue was chromatographed on silica gel using ethyl acetate/petroleum ether (1:4) for the elution. After recrystallization from petroleum ether (boiling point 60°–80° C.) there were obtained 480 mg of 4-(2-methoxyphenyl)-2,2-dimethyl-2H-1-benzopyran-6-carbonitrile of melting point 109°–111° C.

EXAMPLE 60

1.58 g of 4-(4-cyano-2-methoxyphenyl)-2,2-dimethyl-2H-1-benzopyran-6-carbonitrile and 1.05 g of sodium methanethiolate were heated at 100° C. for 20 minutes in 15 ml of dimethylformamide. The mixture was allowed to cool to room temperature and then poured into water and diethyl ether. The aqueous phase was acidified with 2M aqueous hydrochloric acid and extracted with ethyl acetate. The organic extract was washed three times with water, dried over sodium sulphate and evaporated. The residue was chromatographed on silica gel using ethyl acetate/petroleum ether (2:3) for the elution. After o recrystallization of the product from toluene there were obtained 1,1 g of 4-(5-cyano-2-hydroxyphenyl)-2,2-dimethyl-2H-1-benzopyran-6-carbonitrile of melting point 213°-215° C.

The 4-(4-cyano-2-methoxyphenyl)-2,2-dimethyl-2H-1-benzopyran-6-carbonitrile used as the starting material was prepared as follows: (A) 5.18 g of 3-iodo-4-methoxybenzonitrile were added at room temperature to a solution of 18 mg of palladium(II) chloride, 52 mg of triphenylphosphine and 38 mg of copper(I) iodide in 100 ml of diethylamine. 3.7 g of 4-(1,1-dimethyl-2-propynyloxy)benzonitrile were added and the mixture was stirred under a nitrogen atmosphere for 2 days. The mixture was evaporated and the residue was dissolved in ethyl acetate and water. The organic phase was dried over sodium sulphate and evaporated. The residue was chromatographed on silica gel using ethyl acetate/petroleum ether (1:2) for the elution to give 4.8 g of 3-[3-(4-cyanophenoxy)-3-methyl-1-butyn-1-yloxy]-4-methoxybenzonitrile as a solid which was used without further purification. (B) 4.8 g of 3-[3-(4-cyanophenoxy)-3-methyl-1-butyn-1-yloxy]-4-methoxybenzonitrile was heated at reflux for 2.5 hours in 50 ml of 1,2-dichlorobenzene and then allowed to cool to room temperature. The mixture was evaporated and the residue was chromatographed on silica gel using ethyl acetate/petroleum ether (1:2) for the elution. The product was recrystallized from isopropanol to give 3.8 g of 4-(4-cyano-2-methoxyphenyl)-2,2-dimethyl-2H-1-benzopyran-6-carbonitrile of melting point 137°-139° C.

EXAMPLE 61

400 mg of 3-(6-cyano-3,4-dihydro-2,2-dimethyl-2H-1-benzopyran-4-yl)pyridine N-oxide were dissolved in 10 ml of acetic anhydride and heated at reflux for 8 hours. After removal of the solvent by evaporation the residue was dissolved in ethanol and 15 mg of 80% (w/w) sodium hydride were added. After stirring for 30 minutes the mixture was evaporated and the residue was dissolved in a mixture of ethyl acetate and water. The aqueous phase was acidified with dilute hydrochloric acid, extracted with ethyl acetate, then made basic with sodium bicarbonate solution and re-extracted with ethyl acetate. The combined organic extracts were dried over sodium sulphate and evaporated. The residue was chromatographed on silica gel using 8% (v/v) methanol/ethyl acetate for the elution to give 310 mg of 3-(6-cyano-3,4-dihydro-2,2-dimethyl-2H-1-benzopyran-4-yl)-2(1H)-pyridone of melting point 196°-197° C. after recrystallization from t-butyl methyl ether.

The 3-(6-cyano-3,4-dihydro-2,2-dimethyl-2H-1-benzopyran-4-yl)pyridine N-oxide used as the starting material was prepared as follows: (A) 10.25 g of 3-iodopyridine were added at room temperature to a solution of 44 mg of palladium(II) chloride, 131 mg of triphenylphosphine and 95 mg of copper(I) iodide in 200 mg of diethylamine. 9.25 g of 4-(1,1-dimethyl-2-propynyloxy)benzonitrile were then added and the mixture was stirred for 3 days. The mixture was evaporated and the residue was partitioned between ethyl acetate and water. The organic phase was dried over sodium sulphate and evaporated. The residue was chromatographed on silica gel using ethyl acetate/petroleum ether (11:9) for the elution to give 11.8 g of 4-[1,1-dimethyl-3-(3-pyridyl)-2-propynyloxy]benzonitrile in the form of an oil. (B) 11.8 g of 4-[1,1-dimethyl-3-(3-pyridyl)-2-propynyloxy]benzonitrile were heated at reflux in 75 ml of 1,2-dichlorobenzene for 3.5 hours. The reaction mixture was allowed to cool to room temperature and was then evaporated. The residue was chromatographed on silica gel using ethyl acetate for the elution. After recrystallization from cyclohexane there were obtained 6.7 g of 2,2-dimethyl-4-(3-pyridyl)-2H-1-benzopyran-6-carbonitrile of melting point 98°-99° C. (C) 2.1 g of 2,2-dimethyl-4-(3-pyridyl)-2H-1-benzopyran-6-carbonitrile were dissolved in 50 ml of ethyl acetate and shaken at room temperature under a hydrogen atmosphere with 50 mg of 10% palladium-on-charcoal for a total of 30 hours with several changes of catalyst. The mixture was filtered and the filtrate was evaporated. The residue was chromatographed on silica gel using ethyl acetate for the elution. 910 mg of 3,4-dihydro-2,2-dimethyl-4-(3-pyridyl)-2H-1-benzopyran-6-carbonitrile were obtained in the form of an oil. (D) 610 mg of m-chloroperbenzoic acid were added to a solution of 792 mg of 3,4-dihydro-2,2-dimethyl-4-(3-pyridyl)-2H-1-benzopyran-6-carbonitrile in 15 ml of dichloromethane. After stirring at room temperature for one hour the mixture was washed with sodium bisulphite solution and sodium bicarbonate solution. The organic phase was dried over sodium sulphate and evaporated. The residue was crystallized from t-butyl methyl ether to give 710 mg of 3-(6-cyano-3,4-dihydro-2,2-dimethyl-2H-1-benzopyran-4-yl)pyridine N-oxide in the form of a solid of melting point 134°-137° C.

EXAMPLE 62

0.95 g of aluminum chloride was added at 0° C. to 0.6 g of 4-(2,2-dimethyl-2H-1-benzopyran-4-yl)-3-pyridinol in 50 ml of nitromethane. The mixture was stirred for 5 minutes and then 0.51 ml of acetyl chloride was added at 0° C. After stirring at 0° C. for a further 15 minutes and at 20° C. for 15 minutes the solvent was removed by evaporation and the residue was partitioned between ethyl acetate and dilute aqueous sodium hydroxide solution. The organic phase was dried over sodium sulphate and evaporated. The residue was dissolved in ethanol and treated with 0.1 g of a 60% suspension of sodium hydride in mineral oil. After stirring for 20 minutes the solvent was removed by evaporation and the residue was partitioned between water and ethyl acetate. The aqueous phase was acidified with acetic acid and extracted with ethyl acetate. The organic extract was dried and evaporated to give 270 mg of an oil. This oil was dissolved in ethanolic hydrogen chloride and the solution was evaporated. The residue was recrystallized from isopropanol to give 4-(6-acetyl-2,2-dimethyl-2H-1-benzopyran-4-yl)-3-pyridinol hydrochloride of melting point 229°-231° C. (decomposition).

EXAMPLE 63

0.66 g of N,N,N',N'-tetramethylethylenediamine was added to 30 ml of tetrahydrofuran and the mixture was cooled to −78° C. 2.3 ml of a 2.5M solution of n-butyllithium in n-hexane were added, the mixture was stirred at 78° C. for 10 minutes and then 1 g of 3-(N,N-diethylcarbamoyloxy)pyridine in 5 ml of tetrahydrofuran were added. After a further 50 minutes at −78° C. 1 g of 2,2-dimethylchromanone in 5 ml of tetrahydrofuran were added dropwise while stirring and the mixture was held at −78° C. for 1 hour and then allowed to warm to room temperature. The solvent was removed by evaporation and the residue was shaken with water and ethyl acetate. The organic phase was dried over sodium sulphate and evaporated. The residue was chromatographed on silica gel using acetone/petroleum ether (1:1) for the elution to yield 60 mg of 4-(2,2-dimethyl-2H-1-benzopyran-4-yl)-3-pyridinol of melting point 228°–230° C. after recrystallization from isopropanol. The following Examples illustrate typical pharmaceutical preparations containing the compounds of the invention:

EXAMPLE A

Tablets containing the following ingredients may be prepared in a conventional manner:

| Ingredient | Per tablet |
| --- | --- |
| Compound of formula I | 5 mg |
| Lactose | 125 mg |
| Maize starch | 65 mg |
| Talc | 4 mg |
| Magnesium stearate | 1 mg |
| Tablet weight | 200 mg |

EXAMPLE B

Capsules containing the following ingredients may be prepared in a conventional manner:

| Ingredient | Per capsule |
| --- | --- |
| Compound of formula I | 10 mg |
| Lactose | 165 mg |
| Maize starch | 20 mg |
| Talc | 5 mg |
| Capsule fill weight | 200 mg |

We claim:

1. A compound of the formula

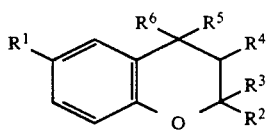

I wherein $R^1$ is hydrogen, halogen, trifluoromethyl, nitro, cyano, lower alkyl, lower alkoxycarbonyl, lower alkylthio, lower alkylsulphonyl, lower alkanoyl, aroyl, carbamoyl, mono(lower alkyl)carbamoyl or di(lower alkyl)carbamoyl, $R^2$ is hydrogen, lower alkyl or phenyl, $R^3$ is hydrogen or lower alkyl, $R^4$ and $R^5$ each is hydrogen or $R^4$ is hydroxy and $R^5$ is hydrogen or $R^4$ and $R^5$ together are a carbon-carbon bond and $R^6$ is unsubstituted 2-hydroxyphenyl, 2-hydroxynaphthyl, 2-pyrazinyl 1-oxide, 2-pyramidinyl 1-oxide, 2-quinolyl 1-oxide; 2-hydroxy phenyl, or 2-hydroxy naphthyl substituted with one or more substituents selected from halogen, cyano and lower alkyl; or 2-pyrazinyl 1-oxide, 2-pyrimidinyl 1-oxide or 2-quinolyl 1-oxide substituted with one or more substituents selected from halogen, amino, hydroxy, benzyloxy, phenyl, (lower alkyl)-phenyl, lower alkyl, lower alkoxy and lower alkoxy carbonyl, or a pharmaceutically acceptable salt of a basic compound of formula I.

2. A compound according to claim 1, wherein $R^1$ is hydrogen, halogen, nitro, cyano, lower alkyl, lower alkoxycarbonyl, lower alkylthio, lower alkyl-sulphonyl, lower alkanoyl, carbamoyl, mono(lower alkyl)-carbamoyl or di(lower alkylcarbamoyl), $R^2$ and $R^3$ each is hydrogen or lower alkyl and $R^4$ and $R^5$ each is hydrogen or together are a carbon-carbon bond.

3. A compound according to claim 1, wherein $R^1$ is nitro, cyano or lower alkanoyl.

4. A compound according to claim 3, wherein $R^1$ is nitro, cyano or acetyl.

5. A compound according to claim 1, wherein $R^2$ and $R^3$ each is lower alkyl.

6. A compound according to claim 5, wherein $R^2$ and $R^3$ each is methyl.

7. A compound according to claim 1, wherein $R^4$ and $R^5$ each is hydrogen or $R^4$ and $R^5$ together are a carbon-carbon bond.

8. A compound according to claim 1, wherein $R^6$ is 2-pyrazinyl 1-oxide, 2-pyrimidinyl 1-oxide or 2-quinolyl 1-oxide.

9. A compound of the formula

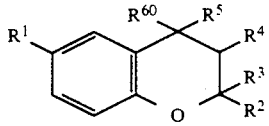

II wherein $R^1$ is hydrogen, halogen, trifluoromethyl, nitro, cyano, lower alkyl, lower alkoxycarbonyl, lower alkylthio, lower alkylsulphonyl, lower alkanoyl, aroyl, carbamoyl, mono(lower alkyl)carbamoyl or di(lower alkyl)carbamoyl, $R^2$ is hydrogen, lower alkyl or phenyl, $R^3$ is hydrogen or lower alkyl, $R^4$ and $R^5$ each is hydrogen or $R^4$ is hydroxy and $R^5$ is hydrogen or $R^4$ and $R^5$ together are a carbon-carbon bond and $R^{60}$ is phenyl or naphthyl, carrying a lower alkoxy group in the 2-position unsubstituted or substituted with one or more substituents selected from halogen, cyano and lower alkyl.

10. A compound of the formula

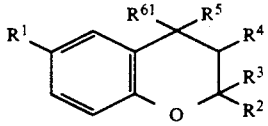

III wherein $R^1$ is hydrogen, halogen, trifluoromethyl, nitro, cyano, lower alkyl, lower alkoxycarbonyl, lower alkylthio, lower alkylsulphonyl, lower alkanoyl, aroyl, carbamoyl, mono(lower alkyl)carbamoyl or di(lower alkyl)carbamoyl, $R^2$ is hydrogen, lower alkyl or phenyl, $R^3$ is hydrogen or lower alkyl, $R^4$ and $R^5$ each is hydrogen or $R^4$ is hydroxy and $R^5$ is hydrogen or $R^4$ and $R^5$ together are a carbon-carbon bond and $R^{61}$ is a pyrazinyl, pyrimidinyl or quinolyl having a nitrogen atom in the 2-position unsubstituted or substituted with one or more substituents selected from halogen, amino, hydroxy, benzyloxy, phenyl, (lower alkyl) phenyl, lower alkyl, lower alkoxy and lower alkoxycarbonyl.

11. A compound of the formula

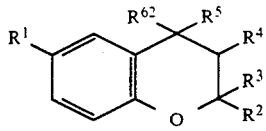

IV wherein $R^1$ is hydrogen, halogen, trifluoromethyl, nitro, cyano, lower alkyl, lower alkoxycarbonyl, lower alkylthio, lower alkylsulphonyl, lower alkanoyl, aroyl, carbamoyl, mono(lower alkyl)carbamoyl or di(lower alkyl)carbamoyl, $R^2$ is hydrogen, lower alkyl or phenyl, $R^3$ is hydrogen or lower alkyl, $R^4$ and $R^5$ each is hydrogen or $R^4$ is hydroxy and $R^5$ is hydrogen or $R^4$ and $R^5$ together are a carbon-carbon and $R^{62}$ is a pyrazinyl, pyrimidinyl or quinolyl having a carbon atom in the 2-position and carrying a N-oxide group in the 3-position unsubstituted or substituted with one or more substituents selected from halogen, amino, hydroxy, benzyloxy, phenyl, (lower alkyl) phenyl, lower alkyl, lower alkoxy and lower alkoxycarbonyl.

12. A compound of the formula

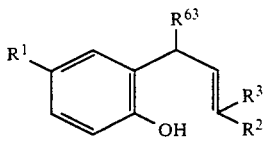

V wherein $R^1$ is hydrogen, halogen, trifluoromethyl, nitro, cyano, lower alkyl, lower alkoxycarbonyl, lower alkylthio, lower alkylsulphonyl, lower alkanoyl, aroyl, carbamoyl, mono(lower alkyl)carbamoyl, or di(lower alkyl)carbamoyl, $R^2$ is hydrogen, lower alkyl and $R^{63}$ is a pyrazinyl, pyrimidinyl or quinolyl carrying a N-oxide group in the 2-position unsubstituted or substituted with one or more substituents selected from halogen, amino, hydroxy, benzyloxy, phenyl, (lower alkyl) phenyl, lower alkyl, lower alkoxy and lower alkoxycarbonyl.

13. A composition for controlling or preventing hypertension, congestive heart failure, angina pectoris, peripheral and cerebral vascular disease, or smooth muscle disorders which comprises an effective amount of a compound of claim 1 or a pharmaceutically acceptable acid addition salt of a basic compound of claim 1, and a pharmaceutically inert inorganic or organic excipient.

14. A method of treating or preventing hypertension, congestive heart failure, angina pectoris, peripheral and cerebral vascular disease and smooth muscle disorders which comprises administering to a patient requiring such treatment an effective amount of a compound of claim 1, or a pharmaceutically acceptable acid addition salt of a basic compound of claim 1.

15. A compound according to claim 2, selected from the group consisting of:
2-(6-cyano-3,4-dihydro-2,2-dimethyl-2H-1-benzopyran-4-yl)pyrimidine 1-oxide,
2-(6-cyano-2,2-dimethyl-2H-1-benzopyran-4-yl)quinoline 1-oxide,
2-(6-cyano-3,4-dihydro-2,2-dimethyl-2H-1-benzopyran-4-yl)quinoline 1-oxide,
4-(2-hydroxyphenyl)-2,2-dimethyl-2H-1-benzopyran-6-carbonitrile, and
4-(5-cyano-2-hydroxyphenyl)-2,2-dimethyl-2H-1-benzopyran-6-carbonitrile.

16. A compound according to claim 1, selected from the group consisting of:
6-(6-cyano-3,4-dihydro-2,2-dimethyl-2H-1-benzopyran-4-yl)pyrimidine 1-oxide and
2-(6-cyano-3,4-dihydro-2,2-dimethyl-2H-1-benzopyran-4-yl)pyrazine 1-oxide.

* * * * *